(12) United States Patent
Cho et al.

(10) Patent No.: US 10,398,529 B2
(45) Date of Patent: Sep. 3, 2019

(54) SENSOR MODULE AND WEARABLE BODY COMPOSITION ANALYZER INCLUDING SAME

(71) Applicant: Samsung Electronics Co., Ltd., Suwon-si (KR)

(72) Inventors: Chul-Ho Cho, Seongnam-si (KR); Kwang-Bok Kim, Incheon (KR); Seong-Je Cho, Suwon-si (KR); Young-Kyu Cho, Seoul (KR); Seung-Min Lee, Seoul (KR); Jeong-Gun Lee, Seoul (KR); Sun-Tae Jung, Yongin-si (KR); Jae-Geol Cho, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 400 days.

(21) Appl. No.: 15/001,895

(22) Filed: Jan. 20, 2016

(65) Prior Publication Data

US 2016/0206241 A1    Jul. 21, 2016

(30) Foreign Application Priority Data

Jan. 20, 2015  (KR) .................. 10-2015-0009284

(51) Int. Cl.
*A61B 90/80*      (2016.01)
*A61B 10/00*      (2006.01)
(Continued)

(52) U.S. Cl.
CPC .......... *A61B 90/80* (2016.02); *A61B 5/14521* (2013.01); *A61B 5/14532* (2013.01);
(Continued)

(58) Field of Classification Search
CPC .............. A61B 5/6801; A61B 10/0045; A61B 5/14532; A61B 5/14521; A61B 90/80; A61M 5/172
See application file for complete search history.

(56) References Cited

U.S. PATENT DOCUMENTS 5,036,861 A    8/1991  Sembrowich et al.
7,725,149 B2   5/2010  Peyser et al.
(Continued)

FOREIGN PATENT DOCUMENTS

JP    2014 523793    9/2014
KR    2007-0043768   4/2007
(Continued)

OTHER PUBLICATIONS

Communication with Supplementary European Search Report dated Dec. 5, 2017 corresponding to European Patent Application No. EP 16740344.3.
(Continued)

*Primary Examiner* — Sean P Dougherty
(74) *Attorney, Agent, or Firm* — Nixon & Vanderhye P.C.

(57) ABSTRACT

A wearable body composition analyzer according to various embodiments of the present disclosure may include an induction part for inducing secretion of bodily liquid while being in contact with a body part, a collection part that collects the bodily liquid secreted, a sensor part that detects a body composition from the bodily liquid collected, and a wearable part to which the induction part and the collection part is detachably attached, wherein the wearable part may be worn on a body. The above-described wearable body composition analyzer may be implemented variously according to embodiments.

14 Claims, 22 Drawing Sheets

(51) Int. Cl.
*A61B 5/145* (2006.01)
*A61M 5/172* (2006.01)
*A61B 5/00* (2006.01)

(52) U.S. Cl.
CPC .......... *A61B 5/681* (2013.01); *A61B 10/0045* (2013.01); *A61M 5/172* (2013.01); *A61B 2560/0209* (2013.01); *A61B 2560/0443* (2013.01)

(56) References Cited

U.S. PATENT DOCUMENTS

| | | | |
|---|---|---|---|
| 2005/0106713 A1 | 5/2005 | Phan et al. | |
| 2006/0004271 A1 | 1/2006 | Peyser et al. | |
| 2007/0027383 A1 | 2/2007 | Peyser et al. | |
| 2009/0270704 A1 | 10/2009 | Peyser et al. | |
| 2010/0063372 A1 | 3/2010 | Potts et al. | |
| 2010/0179403 A1 | 7/2010 | Martinsen et al. | |
| 2010/0234702 A1* | 9/2010 | Tokita | A61B 5/14521 600/309 |
| 2010/0234711 A1* | 9/2010 | Sugenoya | A61B 5/14521 600/365 |
| 2011/0144463 A1 | 6/2011 | Pesach et al. | |
| 2011/0275918 A1 | 11/2011 | Yamashita et al. | |
| 2013/0172691 A1 | 7/2013 | Tran | |
| 2013/0197332 A1 | 8/2013 | Lucisano et al. | |
| 2013/0245388 A1* | 9/2013 | Rafferty | A61B 5/112 600/301 |

FOREIGN PATENT DOCUMENTS

| | | |
|---|---|---|
| KR | 2007-0043768 A | 4/2007 |
| KR | 10-0760517 | 9/2007 |
| KR | 10-0760517 B1 | 9/2007 |
| KR | 10 2011 0004845 | 1/2011 |
| WO | 9305703 | 4/1993 |

OTHER PUBLICATIONS

International Search Report dated Apr. 19, 2016 corresponding to International Patent Application No. PCT/KR2016/000275.
Written Opinion of the International Searching Authority dated Apr. 19, 2016 corresponding to International Patent Application No. PCT/KR2016/000275.
Russell Potts, "Correlation Between Sweat Glucose and Blood Glucose in Subjects with Diabetes", Diabetes Technology & Therapeutics, pp. 398-402.
Russell Potts, "Correlation Between Sweat Glucose and Blood Glucose in Subjects with Diabetes", Diabetes Technology & Therapeutics, pp. 398-402, vol. 14, No. 5, 2012.

* cited by examiner

SENSOR MODULE AND WEARABLE BODY COMPOSITION ANALYZER INCLUDING SAME

RELATED APPLICATION(S)

This application claims the priority under 35 U.S.C. § 119(a) to Korean Application Serial No. 10-2015-0009284, which was filed in the Korean Intellectual Property Office on Jan. 20, 2015, the entire content of which is hereby incorporated by reference.

BACKGROUND

Various embodiments of the present disclosure relate to a wearable body composition analyzer, and for example, relate to a body composition analyzer which may be worn on a part of a body.

In general, blood of a body contains various body compositions such as glucose. Carbohydrates within foods eaten by people are decomposed to glucose through a digestive process. Such glucose, which is a basic energy source of a body, is used as an energy source necessary for various tissues such as the brain, the muscle, and the fat, and is transferred to various tissues through blood of a user. Further, glucose within blood is called blood sugar, and the blood sugar level is increased after a meal, and the blood sugar level is lowered on an empty stomach. Such a blood sugar level is maintained within a predetermined range by an interaction between hormones such as insulin and glucagon secreted by pancreas. When the blood sugar level is increased, insulin restrains glucose from being newly produced by the liver, and increases the use of glucose by muscle tissues and fat tissues, thereby decreasing the blood sugar level. In contrast, when the blood sugar level is decreased, secretion of glucagon is increased, and a production amount of new glucoses by the liver is increased so that the blood sugar level is increased.

A state, in which the blood sugar level deviates from a normal range or the blood sugar level is increased, is called diabetes, which is a type of metabolic diseases. Symptoms of a diabetic patient generally include a high blood sugar level, polyuria signified by an increased amount of urination, polydipsia signified by abnormal amount of water intake, infectious, eyesight abnormality resulting from microvascular complications, kidney function abnormality, peripheral neuritis, foot ulcer, and diseases related to the digestive system, urogenital system, and cardiovascular system as a result of decreasing functionality of the autonomic nervous system. In order to adjust the blood sugar of the diabetic patient, an oral medication such as an insulin secretagogue is used, or insulin is directly injected into a body using a syringe. A dose of the oral medication or an amount of injected insulin is adjusted according to the blood sugar level of the diabetic patient. Further, in order to identify the blood sugar level of the diabetic patient, the diabetic patient periodically measures the blood sugar level thereof using a blood sugar measurement device.

In order to conveniently measure the blood sugar level of the diabetic patient, the blood sugar measurement device should be miniaturized and lightened and may have a design suitable for carrying.

SUMMARY

In general, a blood sugar measurement device for a diabetic patient collects blood from a finger using a lancet, and measures the blood sugar level of the collected blood using a strip sensor and a reader. Diabetic patients, who should measure blood sugar thereof, experience pain caused by a lancet several times per day. To this end, a carry-on bag for carrying the lancet, a disposable strip and a self-blood sugar measurement apparatus are separately necessary. Further, there is a method of measuring blood sugar by causing a needle-type sensor having a diameter of tens of micrometers to be inserted into a body and extracting body fluid in order to minimize the pain caused by the lancet. However, the patients may be infected through an invasive site of a sensor, and large costs are consumed for manufacturing the needle-type sensor having a diameter of tens of micrometers.

Further, a technology is proposed in which an optical analysis method is used as a noninvasive blood sugar measurement scheme which does not use a lancet. However, since the accuracy of a general optical analysis method is lower than the accuracy of the existing blood sugar measurement device, a technology using the optical analysis method has been used within a limited range in which an ordinary person is distinguished from a diabetic patient are distinguished.

Thus, various embodiments of the present disclosure are to provide a wearable body composition analyzer which reduces pain and concern of infection by a lancet using a noninvasive blood sugar measurement scheme.

Further, various embodiments of the present disclosure are to provide a wearable body composition analyzer having an improved portability.

A wearable body composition analyzer according to various embodiments of the present disclosure may include: an induction part that induces a secretion of a bodily liquid while being in contact with a body part, such as, for example, the skin; a collection part that collects the bodily liquid secreted; a sensor part that detects a body composition from the bodily liquid collected by the collection part; and a wearable part detachably attached to at least one of the induction part and the collection part.

The wearable part may be worn on the body.

The wearable body composition analyzer may further include a driving circuit part for applying a signal to the induction part and the sensor part.

In a wearable body composition analyzer according to various embodiments of the present disclosure, an induction part and a collection part may be easily replaced as the induction part or the collection part is detachably attached to a wearable part. Further, as the wearable part may be worn on a body, it is possible to measure a body composition while easily carrying the body composition analyzer. Further, since a lancet is not used, convenience of a user who wants to analyze a body composition thereof may be improved.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
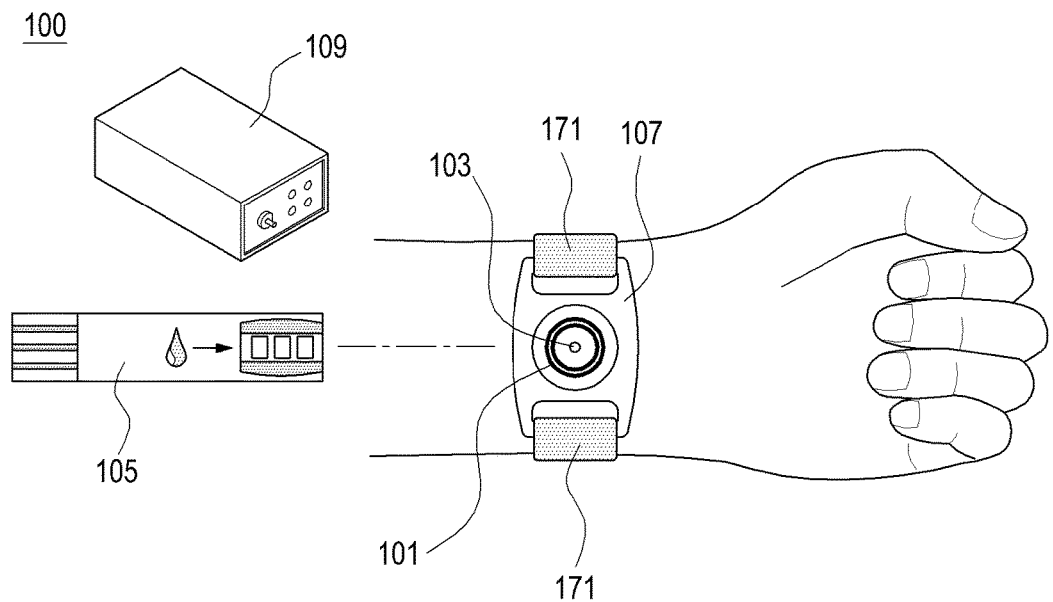
FIG. 1 is a view schematically illustrating a wearable body composition analyzer according to one of various embodiments of the present disclosure.

Hereinafter, various embodiments of the present disclosure will be described with reference to the accompanying drawings. However, it should be understood that there is no intent to limit the present disclosure to the particular forms disclosed herein; rather, the present disclosure should be construed to cover various modifications, equivalents, and/or alternatives of embodiments of the present disclosure. In describing the drawings, similar reference numerals may be used to designate similar constituent elements.

In the present disclosure, the expression "have", "may have", "include" or "may include" refers to existence of a corresponding feature (e.g., numerical value, function, operation, or components such as elements), and does not exclude existence of additional features.

In the present disclosure, the expression "A or B", "at least one of A or/and B", or "one or more of A or/and B" may include all possible combinations of the items listed. For example, the expression "A or B", "at least one of A and B", or "at least one of A or B" refers to all of (1) including at least one A, (2) including at least one B, or (3) including all of at least one A and at least one B.

The expression "a first", "a second", "the first", or "the second" used in various embodiments of the present disclosure may modify various components regardless of the order and/or the importance but does not limit the corresponding components. For example, a first user device and a second user device indicate different user devices although both of them are user devices. For example, a first element may be termed a second element, and similarly, a second element may be termed a first element without departing from the scope of the present disclosure.

It should be understood that when an element (e.g., first element) is referred to as being (operatively or communicatively) "connected," or "coupled," to another element (e.g., second element), it may be directly connected or coupled directly to the other element or any other element (e.g., third element) may be interposer between them. In contrast, it may be understood that when an element (e.g., first element) is referred to as being "directly connected," or "directly coupled" to another element (second element), there are no element (e.g., third element) interposed between them.

The expression "configured to" used in the present disclosure may be exchanged with, for example, "suitable for", "having the capacity to", "designed to", "adapted to", "made to", or "capable of" according to the situation. The term "configured to" may not necessarily imply "specifically designed to" in hardware. Alternatively, in some situations, the expression "device configured to" may mean that the device, together with other devices or components, "is able to". For example, the phrase "processor adapted (or configured) to perform A, B, and C" may mean a dedicated processor (e.g. embedded processor) only for performing the corresponding operations or a generic-purpose processor (e.g., central processing unit (CPU) or application processor (AP)) that may perform the corresponding operations by executing one or more software programs stored in a memory device.

The terms used herein are merely for the purpose of describing particular embodiments and are not intended to limit the scope of other embodiments. As used herein, singular forms may include plural forms as well unless the context clearly indicates otherwise. Unless defined otherwise, all terms used herein, including technical and scientific terms, have the same meaning as those commonly understood by a person skilled in the art to which the present disclosure pertains. Such terms as those defined in a generally used dictionary may be interpreted to have the meanings equal to the contextual meanings in the relevant field of art, and are not to be interpreted to have ideal or excessively formal meanings unless clearly defined in the present disclosure. In some cases, even the term defined in the present disclosure should not be interpreted to exclude embodiments of the present disclosure.

FIG. 1 is a view schematically illustrating a wearable body composition analyzer according to one of various embodiments of the present disclosure.

Referring to FIG. 1, a wearable body composition analyzer 100 according to one of various embodiments of the present disclosure may include an induction part 101, a collection part 103, a sensor part 105, and a wearable part 107. Here, the wearable body composition analyzer 100 may be an electronic device electrically operated. A detailed description for the electronic device will be described below.

The induction part 101 may induce a secretion of a bodily liquid while being in contact with a body part, such as, for example, the skin. Further, the bodily liquid may be sweat secreted from sweat glands of the skin. However, the bodily liquid is not limited to the sweat, and may be various liquid compositions secreted through the skin of the body. Further, the induction part 101 may include an inductive agent stimulating the skin of the body to secrete the bodily liquid. The inductive agent may be pilocarpine or acethylcholine. However, the inductive agent is not limited to pilocarpine or acethylcholine, and may be various materials inducing the secretion of the bodily liquid. Further, the induction part 101 may receive power, and the induction part 101 may dissociate the inductive agent through the received power. The dissociated inductive agent may be absorbed to the skin and then stimulate the skin. For example, the induction part 101 may inject the inductive agent to induce a secretion and a discharge of the bodily liquid from the body. The induction part 101 may have a circular shape as illustrated in FIG. 1. The induction part 101 having a circular form may collect the bodily liquid secreted and discharged from the body, to the interior of the induction part 101. However, the induction part 101 is not limited to have a circular form.

The collection part 103 may collect the bodily liquid secreted. The collection part 103 may be arranged inside the induction part 101. The bodily liquid inside the induction part 101 may be collected to the collection part 103. The collection part 103 may store the collected bodily liquid. Further, the collection part 103 may be manufactured integrally with the induction part 101. Further, the induction part 101 may have a structure mounted to the collection part 103.

The sensor part 105 may be connected to the collection part 103 to detect a body composition from the collected bodily liquid. Further, the body composition may be glucose included in the bodily liquid. That is, the sensor part 105 may detect glucose. The sensor part 105 may have a strip form, but is not limited thereto. Further, the sensor part 105 may have various forms connected to the collection part 103 to be used disposably.

The wearable part 107 may be detachably attached to at least one of the induction part 101 and the collection part 103. Further, the wearable part 107 may be worn on a body. The wearable part 107 may include a band 171 worn on the body, e.g., a wrist. However, the wearable part 107 is not limited to a band form worn on a wrist, and may have various forms which may be worn on the body. Further, the wearable part 107 may be detachably attached to the collection part 103 to which the induction part 101 is mounted. The wearable part 107 may be a groove corresponding to the collection part 103, and the collection part 103 may be fitted in the groove. Further, the induction part 101 may be detachably attached to the wearable part 107, and the induction part 101 may be detachably attached to the collection part 103. In this way, at least one of the induction part 101 and the collection part 103 is detachably attached to the wearable part 107 so that the induction part 101 and the collection part 103 may be replaced. For example, the induction part 101 and the collection part 103 which has collected the bodily liquid, and another induction part 101 and another collection part 103 may be mounted.

Further, data obtained by detecting the body composition may be transmitted to a separate electronic device 109. The separate electronic device 109 may store the collected data, and transmit/receive the data to/from yet another electronic device. A detailed description for the electronic device will be described below.

Figure 2:
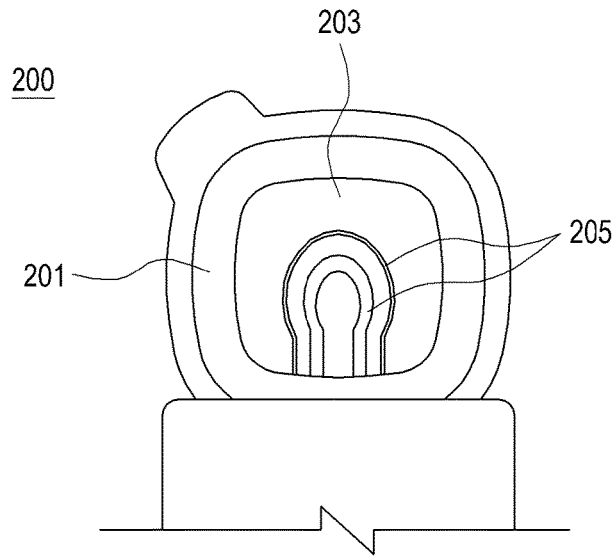
FIG. 2 is a plan view illustrating an induction part and a sensor part of a wearable body composition analyzer according to another one of various embodiments of the present disclosure.

FIG. 2 is a plan view illustrating an induction part and a sensor part of a wearable body composition analyzer according to another one of various embodiments of the present disclosure. Since a wearable body composition analyzer 200 according to another one of various embodiments of the present disclosure is similar to the wearable body composition analyzer 100 according to the above-described embodiment, a detailed description for similar components will be omitted, and a collection part and a sensor part will be mainly described.

Referring to FIG. 2, a collection part 203 and a sensor part 205 applied to the wearable body composition analyzer 200 according to another one of various embodiments of the present disclosure may be integrally manufactured. Further, the induction part 201 may induce a secretion of a bodily liquid while being in contact with the skin. Further, the collection part 203 is formed inside the induction part 201 so as to collect bodily liquid secreted by the induction part 201.

The sensor part 205 may be arranged inside the collection part 203. Accordingly, in the wearable body composition analyzer 200 according to another one of various embodiments of the present disclosure, it is unnecessary that a sensor part is not separately carried and the sensor part is not connected to the collection part, so that the wearable body composition analyzer 200 may be conveniently used.

Figure 3:
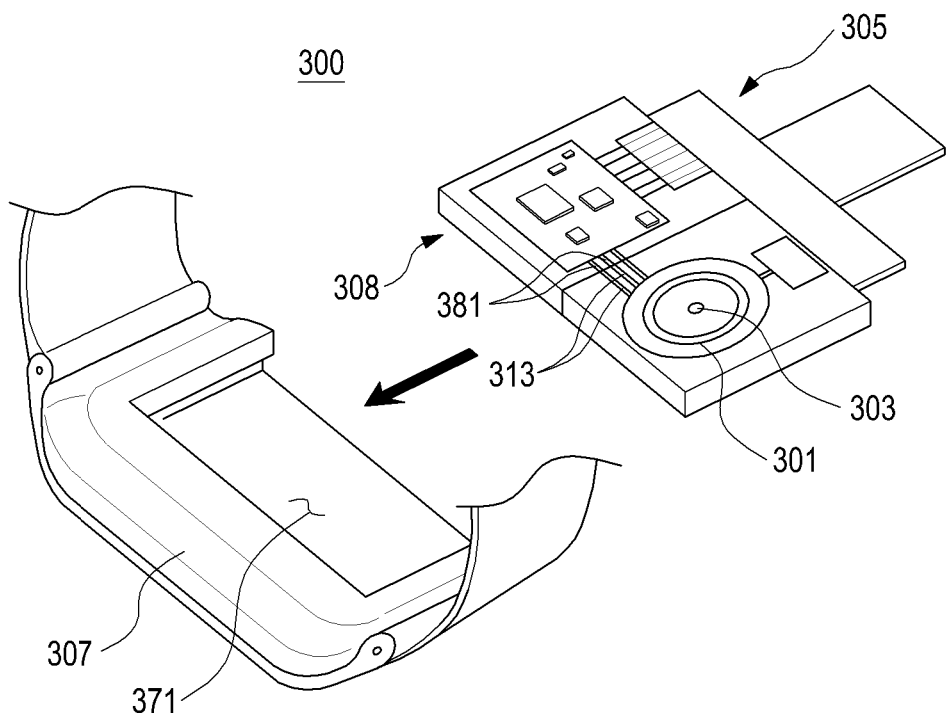
FIG. 3 is a perspective view illustrating a wearable body composition analyzer according to yet another one of various embodiments of the present disclosure.
Figure 4:
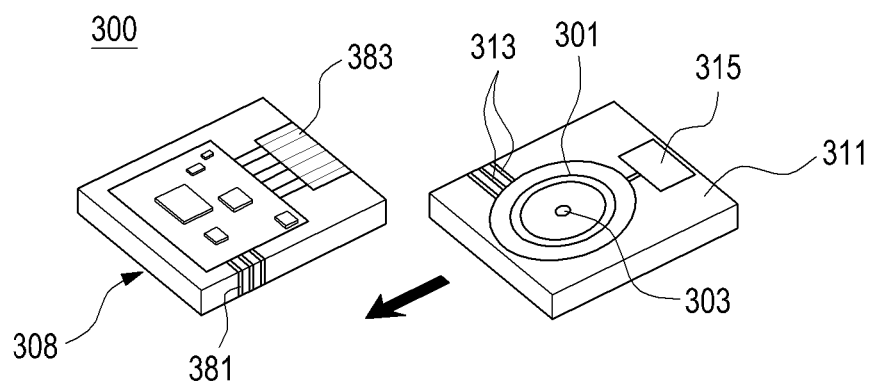
FIG. 4 is a perspective view illustrating a state in which an induction body part of FIG. 3 is connected to a driving circuit part.
Figure 5:
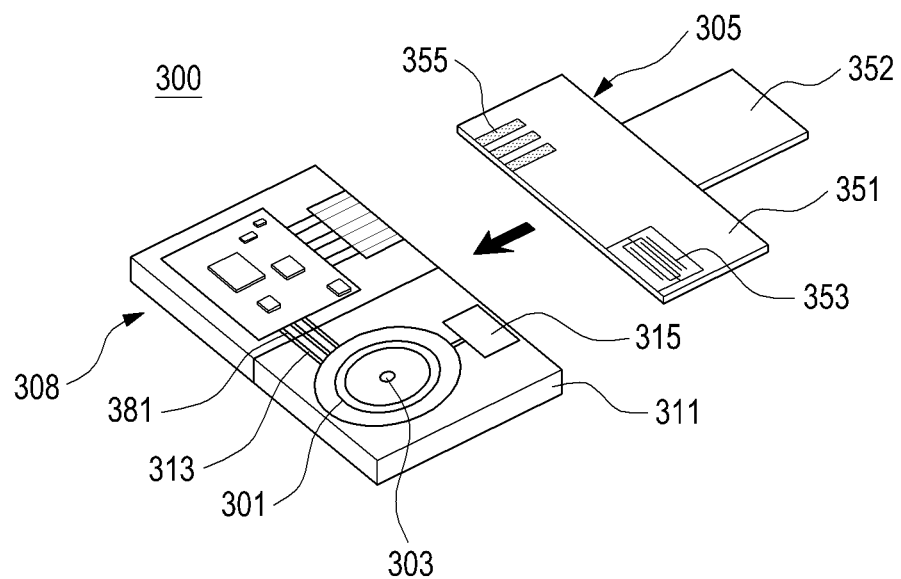
FIG. 5 is a perspective view illustrating a state in which a sensor part of FIG. 3 is connected to the induction body part and the driving circuit part.

FIG. 3 is a perspective view illustrating a wearable body composition analyzer according to yet another one of various embodiments of the present disclosure. FIG. 4 is a perspective view illustrating a state in which an induction body part of FIG. 3 is connected to a driving circuit part. FIG. 5 is a perspective view illustrating a state in which a sensor part of FIG. 3 is connected to the induction body part and the driving circuit part.

Referring to FIGS. 3 to 5, a wearable body composition analyzer 300 according to yet another one of various embodiments of the present disclosure may include an induction body part 311, an induction part 301, a collection part 303, a sensor part 305, a driving circuit part 308, and a wearable part 307.

The induction body part 311 may include the induction part 301 and the collection part 303. The induction body part 311 may include a wiring part 313 for electrically connecting the induction part 301 to the driving circuit part 308. Further, the induction body part 311 may include a first collection connection part 315 that connects the collection part 303 to the sensor part 305.

The induction part 301 is formed in the induction body part 311 and may induce a secretion of the bodily liquid while being in contact with the skin. The induction part 301 may be electrically connected to the driving circuit part 308 which will be described below. The induction part 301 may receive current from the driving circuit part 308 to supply the current to the skin. The induction part 301 may stimulate the skin by the current to induce a secretion of a bodily liquid.

The collection part 303 may be arranged inside the induction part 301. The collection part 303 may collect bodily liquid secreted by the induction part 301.

The sensor part 305 may detect a body composition from the bodily liquid collected by the collection part 303. The sensor part 305 may include a second collection connection part 353 connected to the first collection connection part 315. As the second collection connection part 353 is connected to the first collection connection part 315, the sensor part 305 may detect a body composition from the bodily liquid collected by the collection part 303. The sensor part 305 may include a signal connection part 355 electrically connected to the driving circuit part 308.

The driving circuit part 308 may apply a signal to the induction part 301 and the sensor part 305. The driving circuit part 308 may include a first connection part 381 and a second connection part 383. The first connection part 381 may connect the driving circuit part 308 and the induction part 301 while being in contact with the wiring part 313 of the induction part 301. The driving circuit part 308 may adjust power supplied from the induction part 301. The second connection part 383 may connect the driving circuit part 308 to the induction part 301 while being in contact with the signal connection part 355 of the sensor part 305. The driving circuit part 308 may receive a signal of the body composition detected by the sensor part 305 to analyze a body composition of the collected bodily liquid. As the driving circuit part 308 includes the first connection part 381 and the second connection part 383 to be connected to the induction body part 311 and the sensor part 305, another induction body part and another sensor part may be replaced and connected after the induction body part 311 and the sensor part 305 are used.

The wearable part 307 may be worn on the body, and the induction body part 311 may be detachably attached to the driving circuit part 308. That is, the induction part 301 and the collection part 303 formed in the induction body part 311 may be detachably attached to the wearable part 307. The wearable part 307 may have an attachment/detachment groove 371 to/from which the induction body part 311 and the driving circuit part 308 are simultaneously inserted and attached/detached. However, the attachment/detachment groove 371 is not limited to a form in which the induction body part 311 and the driving circuit part 308 are simultaneously inserted thereinto, and may have a form in which at least one of the induction body part 311 and the driving circuit part 308 is inserted thereinto.

In this way, in the wearable body composition analyzer 300 according to yet another one of various embodiments of the present disclosure, the induction part 301, the collection part 303, and the sensor part 305 used by a user are detached from the wearable part 307, are replaced with another induction part, another collection part, an another sensor part, and thus, are mounted to the wearable part 307.

Figure 6:
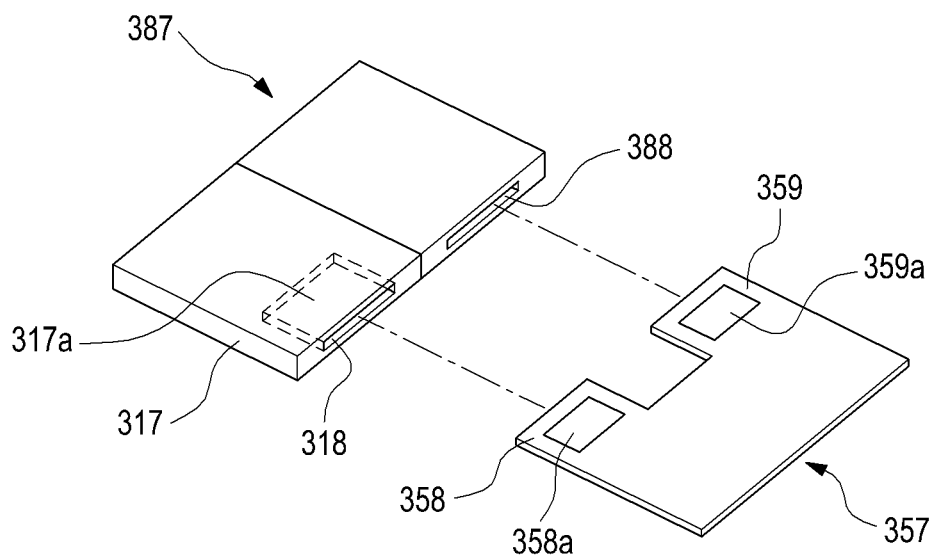
FIG. 6 is a perspective view illustrating a state in which the sensor part applied to the wearable body composition analyzer is detached according to yet another one of various embodiments of the present disclosure.

FIG. 6 is a perspective view illustrating a state in which the sensor part applied to the wearable body composition analyzer is detached according to yet another one of various embodiments of the present disclosure. According to various embodiments of the present disclosure, an induction part 317 may collect secreted bodily liquid while inducing a secretion of the bodily liquid. For example, the induction part 317 may include a collection part according to the above-described embodiment. Further, the bodily liquid collected by the induction part 317 may move to a first collection connection part 317a.

Referring to FIG. 6, a sensor part 357 may be configured by a sensor module form including a first insertion part 358, a second insertion part 359, and a detection part 358a.

The first insertion part 358 and the second insertion part 359 may protrude from the sensor part 357. The first insertion part 358 may include the detection part 358a connected to the first collection connection part 317a of the induction part 317. The bodily liquid collected by the first collection connection part 317a comes into contact with the detection part 358a so that the detection part 358a may detect a body composition from the bodily liquid. The second insertion part 359 may include a signal connection part 359a connected to the driving circuit part 387. The first insertion part 358 may be arranged to be symmetric to the second insertion part 359 on the sensor part 357.

Further, the induction part 317 may include a first insertion groove 318 corresponding to the first insertion part 358. The induction part 317 may be detachably attached to the sensor part 357 as the first insertion part 358 is separatably inserted into the first insertion groove 318. Further, the driving circuit part 387 may include a second insertion groove 388 corresponding to the second insertion part 359. The driving circuit part 387 may be detachably attached to the sensor part 357 as the second insertion part 359 is separatably inserted into the second insertion groove 388. However, the first insertion part 358 and the second insertion part 359 is not limited to protrude, and may have various structures detachably attached to the induction part 317 and the driving circuit part 387.

Further, when the first insertion part 358 and the second insertion part 359 are inserted into and coupled to the first insertion groove 318 and the second insertion groove 388, a state in which the induction part 317 is in contact with the driving circuit part 387 may be maintained even when there is no separate coupling structure between the induction part 317 and the driving circuit part 387. The induction part 317 and the driving circuit part 387 may be detachably attached to the above-described wearable part (e.g., a watch). However, the induction part 317 and the driving circuit part 387 are not limited to be detachably attached to the wearable part, and at least one of the induction part 317 and the driving circuit part 387 may be detachably attached to the wearable part.

Figure 7:
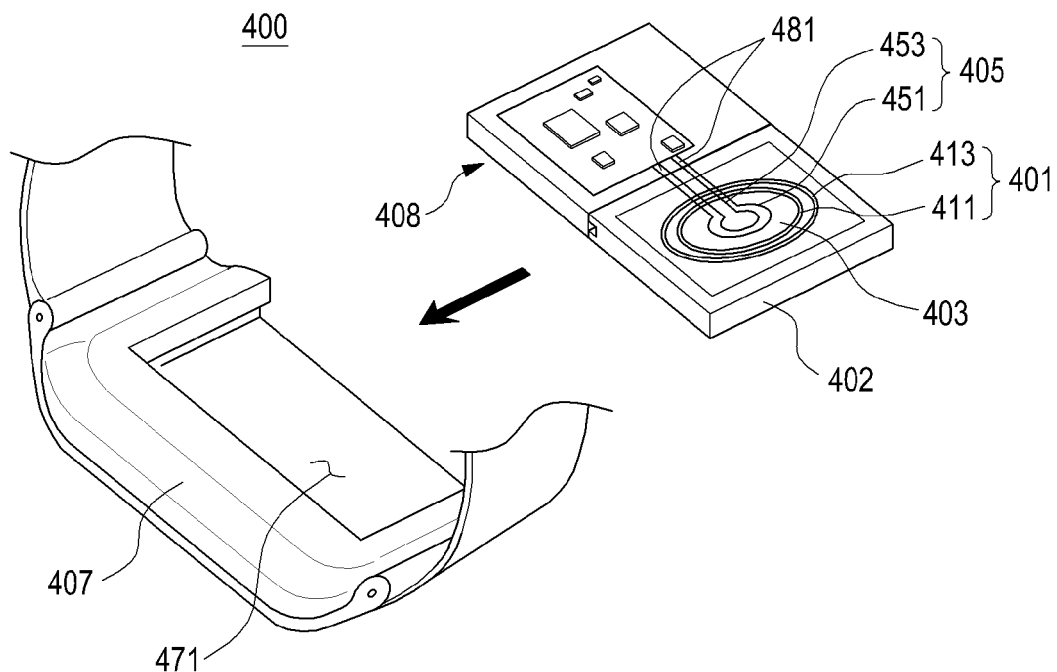
FIG. 7 is a perspective view illustrating a wearable body composition analyzer according to yet another one of various embodiments of the present disclosure.
Figure 8:
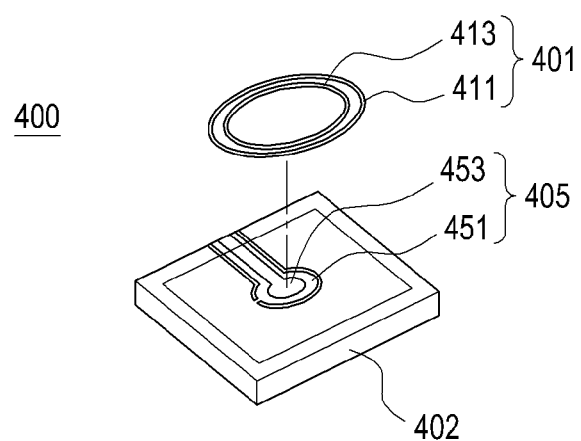
FIG. 8 is a perspective view illustrating a state in which a sensor part of FIG. 7 is connected to the induction body part.

FIG. 7 is a perspective view illustrating a wearable body composition analyzer according to yet another one of various embodiments of the present disclosure. FIG. 8 is a perspective view illustrating a state in which a sensor part of FIG. 7 is connected to the induction body part.

Referring to FIGS. 7 and 8, a wearable body composition analyzer 400 according to yet another one of various embodiments of the present disclosure may include an induction body part 402, an induction part 401, a collection part 403, a sensor part 405, a driving circuit part 408, and a wearable part 407.

The induction body part 402 may include the induction part 401 and the sensor part 405. The sensor part 405 may be arranged on the upper surface of the induction body part 402, and the induction part 401 may be arranged on the upper surface of the induction body part 402 to be located outside of the sensor part. The induction part 401 may be formed in a circular shape. The induction part 401 may induce a secretion of a bodily liquid while being in contact with the skin of a body. The collection part 403 may be arranged inside the induction part 401. The bodily liquid secreted by the induction part 401 may be temporarily stored in the collection part 403. The sensor part 405 is formed inside the collection part 403 so as to detect a body composition from the bodily liquid collected by the collection part 403. The sensor part 405 may be in contact with the first connection wire 481 of the driving circuit part 408. The sensor part 405 may transmit, to the driving circuit part 408, a signal of the detected body composition through the first connection wire 481. The wearable part 407 may have an attachment/detachment groove 471 to/from which the induction body part 402 and the driving circuit part 408 are attached/detached. Accordingly, a user may wear the wearable body composition analyzer 400 to analyze the body composition and then separate the induction body part 402 and the driving circuit part 408 from the wearable part 407. Further, after the induction body part 402 is separated from the driving circuit part 408, and the induction body part 402 including another induction part 401 and another sensor part 405 may be connected to the driving circuit part 408.

In this way, in the wearable body composition analyzer 400 according to various embodiments of the present disclosure, as the induction body part 402 integrally includes the induction part 401 and the sensor part 405, a user needs not to separately detach the sensor part so that convenience of use is improved.

Figure 9:
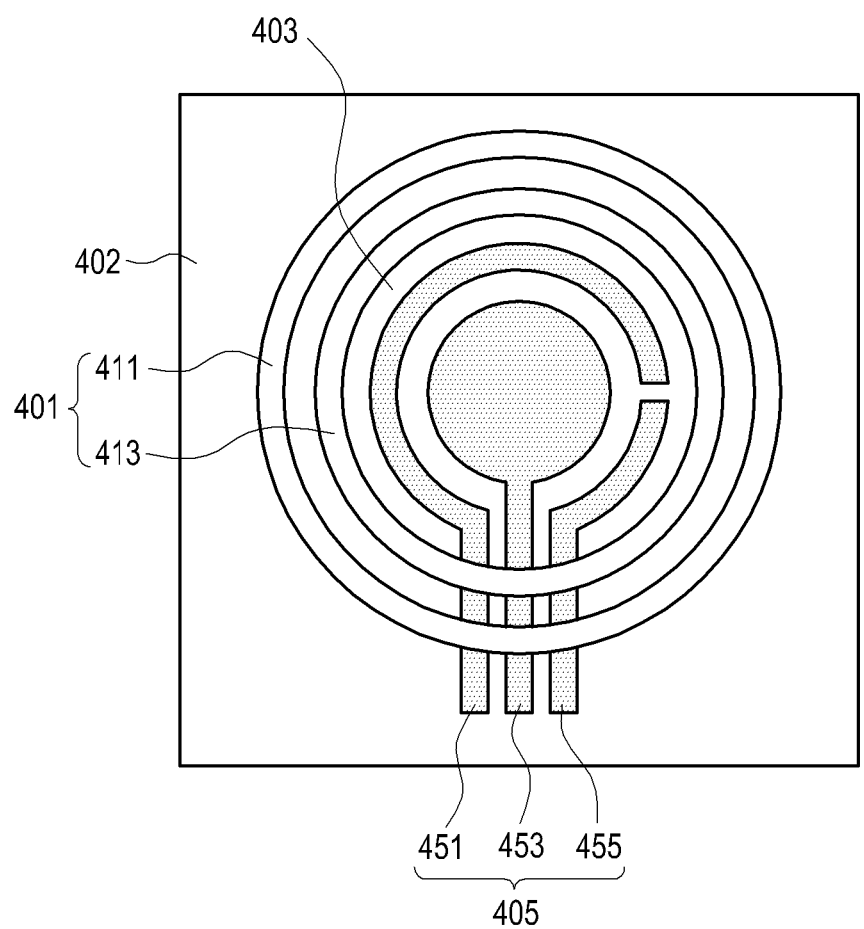
FIG. 9 is a plan view illustrating an induction part and a sensor part of FIG. 8.
Figure 10:
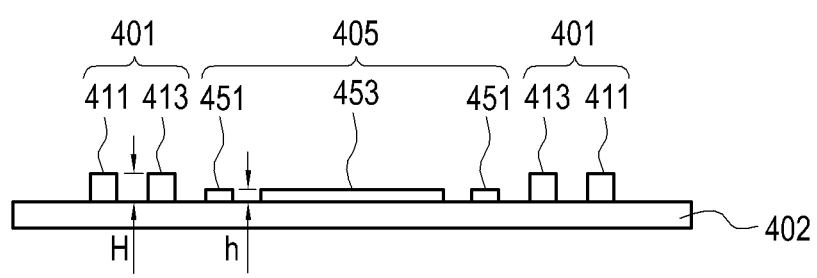
FIG. 10 is a side view illustrating the induction part and the sensor part of FIG. 8.

FIG. 9 is a plan view illustrating an induction part and a sensor part of FIG. 8. FIG. 10 is a side view illustrating the induction part and the sensor part of FIG. 8.

Referring to FIGS. 9 to 10, the sensor part 405 may include an operation electrode 451 and a counter electrode 453.

The operation electrode 451 may be operated by a signal applied from the driving circuit part 408 (FIG. 7). The counter electrode 453 may be arranged inside the operation electrode 451 to be spaced apart from the operation electrode 451. The counter electrode 453 may be electrically connected to the driving circuit part 408 (FIG. 7). However, the operation electrode 451 is not limited to be arranged outside the counter electrode 453, and the operation electrode 451 may be arranged inside the counter electrode 453. Further, when the body composition exists between the operation electrode 451 and the counter electrode 453, the operation electrode 451 may be electrically connected to the counter electrode 453 by the body composition. That is, the sensor part 405 may detect a current by the body composition between the operation electrode 451 and the counter electrode 453.

Further, the sensor part 405 may further include an auxiliary electrode 455. The auxiliary electrode 455 may be arranged to be spaced apart from the operation electrode 451 and the counter electrode 453. The auxiliary electrode 455 may be electrically connected to the driving circuit part 408 (FIG. 7). Further, when bodily liquid exists between the operation electrode 451 and the auxiliary electrode 455, the auxiliary electrode 455 may be electrically connected to the operation electrode 451 by the body composition. That is, the auxiliary electrode 455 may detect a current flowing between the operation electrode 451 and the auxiliary electrode 455 to determine whether there is the bodily liquid. Accordingly, the driving circuit part 408 (FIG. 7) may allow a first current or a second current to flow on the operation electrode 451. When bodily liquid exists between the operation electrode 451 and the auxiliary electrode 455, the first current may be a current necessary for electrically connecting the operation electrode 451 to the auxiliary electrode 455 through the bodily liquid. When a bodily liquid is present between the operation electrode 451 and the counter electrode 453, the second current may be a current necessary for detecting a body composition included in the bodily liquid. Further, the second current may be larger than the first current. Thus, the driving circuit part 408 (FIG. 7) may apply the first current smaller than the second current to the sensor part 405 until the sensor part 405 detects the bodily liquid. When the operation electrode 451 is electrically connected to the auxiliary electrode 455 via the bodily liquid, the driving circuit part may apply the second current to the operation electrode 451 to analyze a composition (e.g., the body composition) of the bodily liquid. Accordingly, before a sufficient amount of bodily liquid necessary for analyzing the body composition is collected, the driving circuit part 408 (FIG. 7) applies the relatively low first current, thereby improving power consumption used by the sensor part 405.

The induction part 401 may be arranged on the upper surface of the induction body part 402. The induction part 401 may include a first induction part 411 and a second induction part 413. The first induction part 411 may be arranged outside the sensor part 405 and may have a circular shape. The second induction part 413 may be formed between the first induction part 411 and the sensor part 405. The first induction part 411 may be in contact with the skin of a body. The first induction part 411 may receive a current from the driving circuit part 408 (FIG. 7), and the second induction part 413 may be electrically connected to the driving circuit part 408 (FIG. 7). The current supplied to the first induction part 411 may pass through the skin, and then be transferred to the driving circuit part 408 (FIG. 7) by the second induction part 413. However, the first induction part 411 is not limited to receive a current from the driving circuit part 408 (FIG. 7), and in contrast, the second induction part 413 may receive a current from the driving circuit part 408 (FIG. 7). The induction part 401 may include an inductive agent for inducing a secretion of the bodily liquid. The inductive agent may be injected into the skin by an electrical signal applied from the driving circuit part 408 (FIG. 7). The inductive agent may quicken the secretion of the bodily liquid.

As illustrated in FIG. 10, the induction part 401 may have a first height H with respect to the induction body part 402. Further, the sensor part 405 may have a second height h with respect to the induction body part 402. The first height H may be larger than the second height h. The induction part 401 having the first height H may surround the sensor part 405 having the second height h from the outside. When being in contact with the skin, the induction part 401 may function as a barrier for preventing the bodily liquid from being discharged to the outside of the induction part 401. That is, the sensor part 405 may be surrounded by the skin, the induction part 401, and the induction body part 402.

Figure 11:
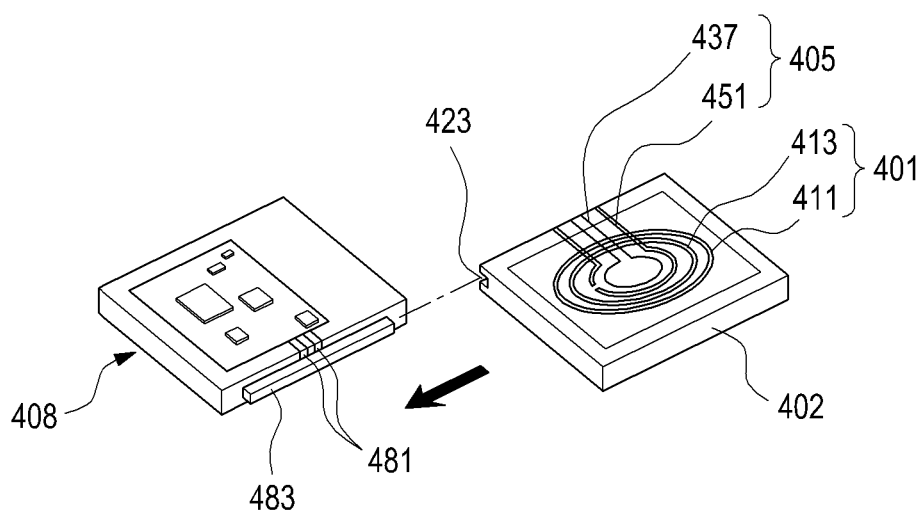
FIG. 11 is a perspective view illustrating a state in which the induction body part is connected to the driving circuit part.

FIG. 11 is a perspective view illustrating a state in which the induction body part is connected to the driving circuit part.

Referring to FIG. 11, the driving circuit part 408 may include a protrusion part 483. The protrusion part 483 may protrude towards the induction body part 402. The induction body part 402 may include a support groove 423 corresponding to the protrusion part 483. The protrusion part 483 may connect the driving circuit part 408 to the induction body part 402 while being inserted into the support groove 423. That is, after the driving circuit part 408 has been connected to the induction body part 402, the driving circuit part 408 and the induction body part 402 may be mounted to the wearable part 407. Further, as the protrusion part 483 is inserted in the support groove 423, the driving circuit part 408 and the induction body part 402 may strengthen the binding between the driving circuit part 408 and the induction body part 402, and stabilize an electrical connection between the driving circuit part 408 and the first connection wire 481.

Figure 12:
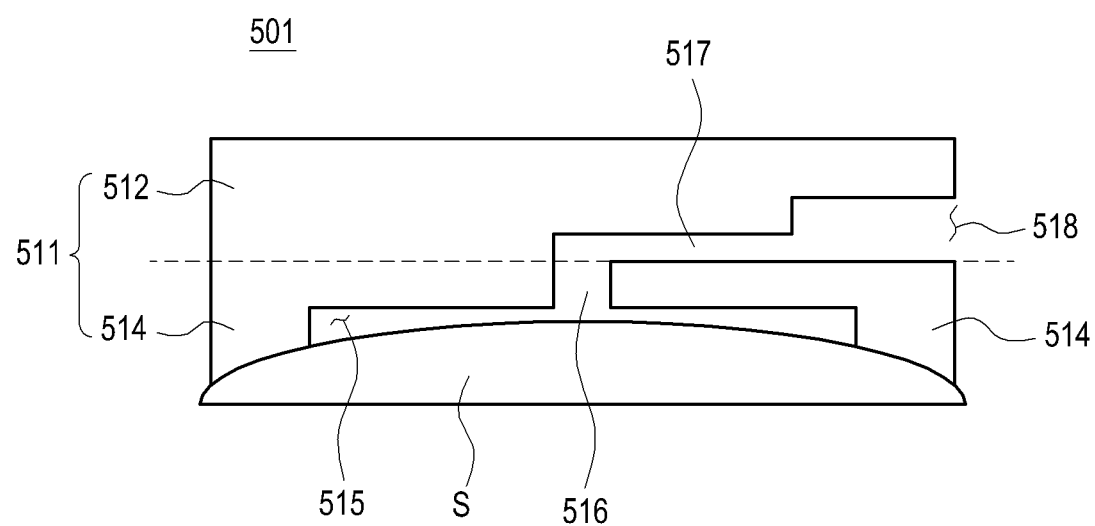
FIG. 12 is a sectional view illustrating a collection part of the wearable body composition analyzer according to yet another one of various embodiments of the present disclosure.

FIG. 12 is a sectional view illustrating a collection part of the wearable body composition analyzer according to yet another one of various embodiments of the present disclosure. A description for components similar to the components of the above-described embodiments from among components of the present embodiment will be omitted, and a collection part will be mainly described.

Referring to FIG. 12, a collection part 501 may include a space provision part 511 which is in contact with a part of the skin and has a collection space 515 formed therein in which secreted bodily liquid is collected, and a movement path part 517 communicating with the collection space 515 to provide the movement path of the bodily liquid.

The space provision part 511 may include a cover part 512 and a contact part 514. A communication opening 516 communicating with the movement path part 517 may be formed in the cover part 512. The bodily liquid collected in the collection space 515 may be moved to the movement path part 517 through the communication opening 516. The contact part 514 may extend from a lower portion of the cover part 512 to be in contact with the skin. Here, the lower portion of the cover part 512 may be defined by a part of the space provision part 511 facing the skin. The contact part 514 may form a closed curve to form the collection space 515. That is, the contact part 514 may form the collection space 515 together with the cover part 512 on the skin.

The movement path part 517 may communicate with the collection space 515 through the communication opening 516 of the cover part 512. The movement path part 517 may provide a path through which the bodily liquid moves to, for example, the above-described sensor part. The movement path part 517 may have a capillary tube shape. Accordingly, the bodily liquid may move the movement path part 517 by a capillary phenomenon even without the provision of a driving force which consumes separate energy.

FIGS. 13 to 16 are sectional views illustrating the induction part of the wearable body composition analyzer according to yet another one of various embodiments of the present disclosure. A description for components similar to the components of the above-described embodiments from among components of the present embodiment will be omitted, and a collection part will be mainly described.

Referring to FIGS. 13 to 16, a collection part 502 may include a space provision part 521 including a cover part 522 and a contact part 524 and a movement path part 527 communicating with the space provision part 521. The space provision part 521 may form a collection space by the cover part 522 and the contact part 524. The cover part 522 may have a communication opening 526 communicating with the collection space 525 and the movement path part 527.

The communication opening 526 may be formed to be adjacent to the contact part 524. The communication opening 526 may be formed to be adjacent to an edge of the collection space 525. For example, the communication opening 526 may be formed to be adjacent to an inner wall of the contact part 524. Thus, even when the skin is introduced into the collection space 525 in a state in which the wearable body composition analyzer is in contact with the skin, it is possible to present the communication opening 526 from being closed. For example, it is possible to prevent a movement path of bodily liquid collected in the collection space 525 from being closed.

A process of moving bodily liquid by the collection part 502 will be described below.

Figure 13:
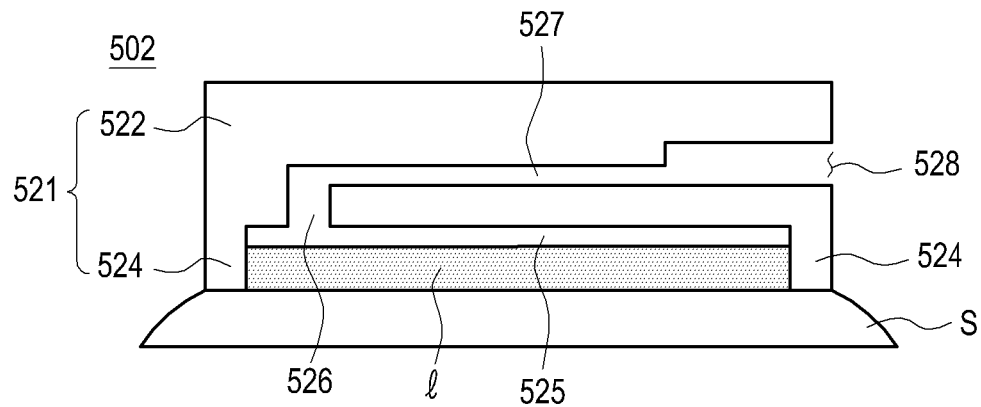
FIGS. 13, 14, 15, and 16 are sectional views illustrating the collection part of the wearable body composition analyzer according to yet another one of various embodiments of the present disclosure.
Figure 14:
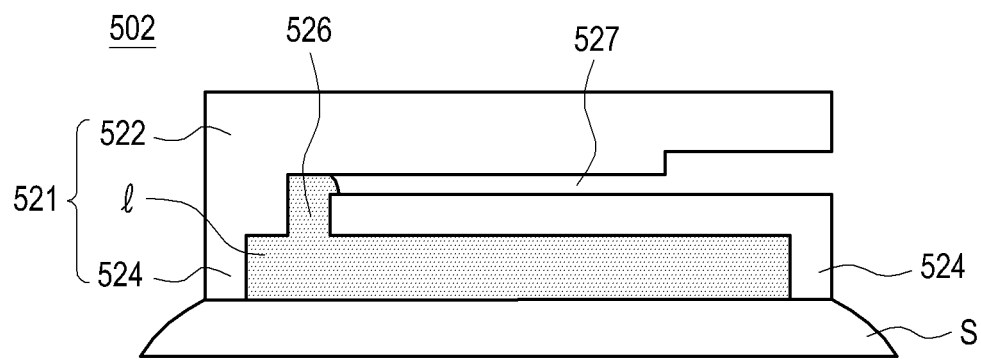
Figure 15:
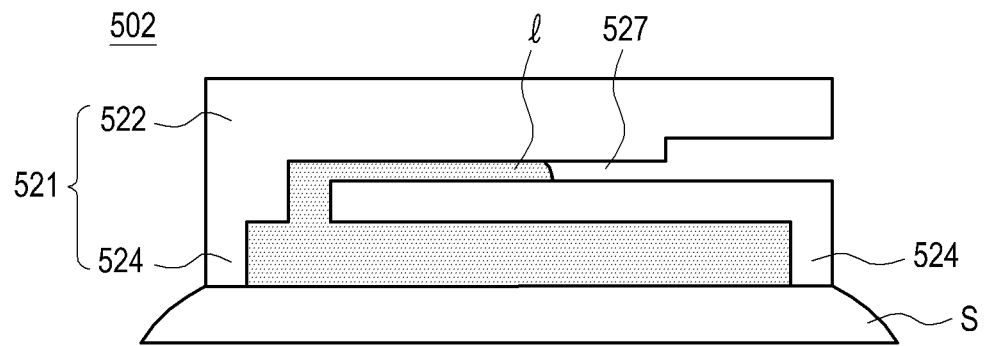

First, as illustrated in FIG. 13, the bodily liquid l may be collected in the collection space 525 on the skin S. Further, as illustrated in FIG. 14, the bodily liquid l may move to the movement path part 527 through the communication opening 526. Next, the bodily liquid l may move along the movement path part 527 by a capillary phenomenon.

Figure 16:
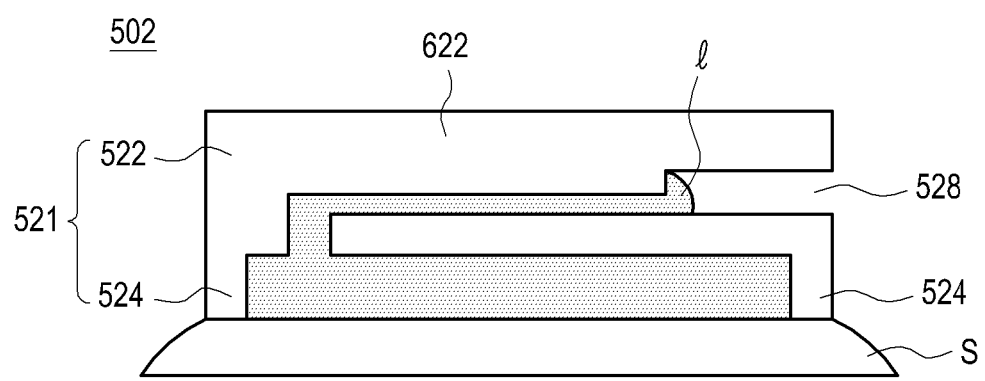

Meanwhile, the movement path part 527 may include a sensor coupling part 528 to which a sensor part is coupled. As illustrated in FIG. 16, the bodily liquid l may be formed at a part where the sensor coupling part 528 firstly extends, in a bubble shape. A process of forming bodily liquid in a bubble shape will be described below with reference to the accompanying drawing.

Figure 17:
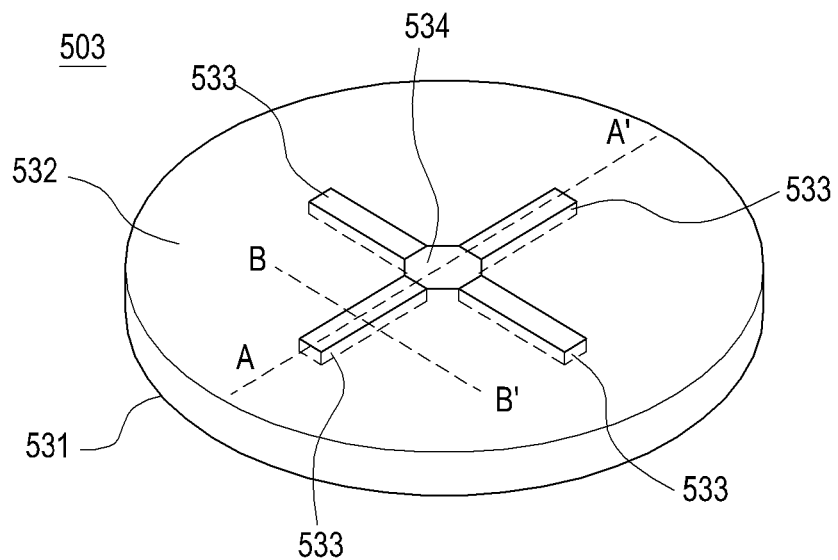
FIG. 17 is a perspective view illustrating the collection part of the wearable body composition analyzer according to yet another one of various embodiments of the present disclosure.
Figure 18:
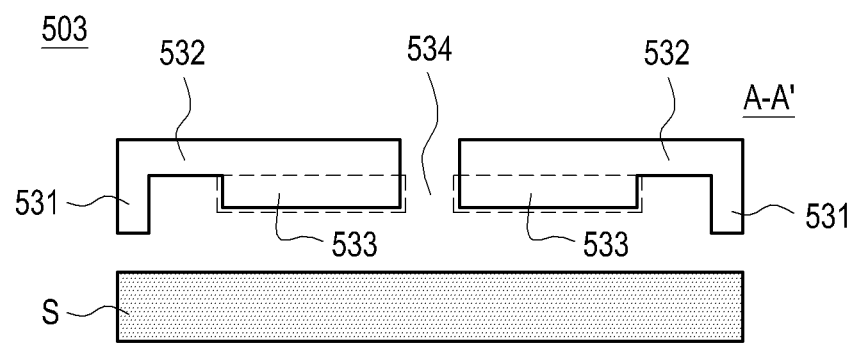
FIG. 18 is a sectional view taken along line A-A' illustrating the collection part of FIG. 17.
Figure 19:
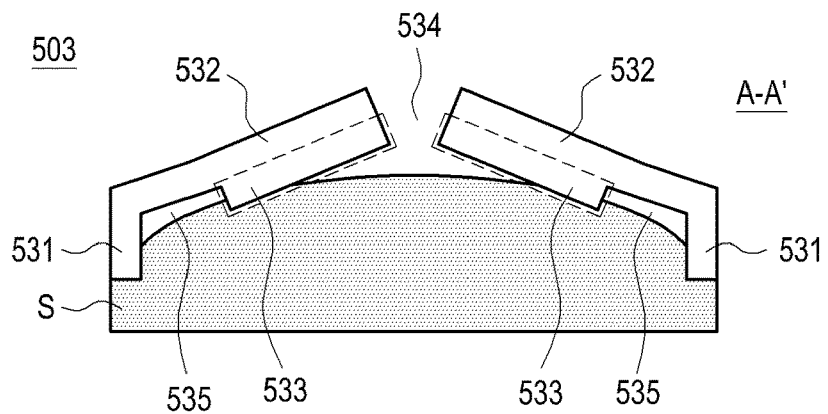
FIG. 19 is a sectional view taken along line A-A' illustrating a state in which the collection part of FIG. 17 is in contact with a skin.
Figure 20:
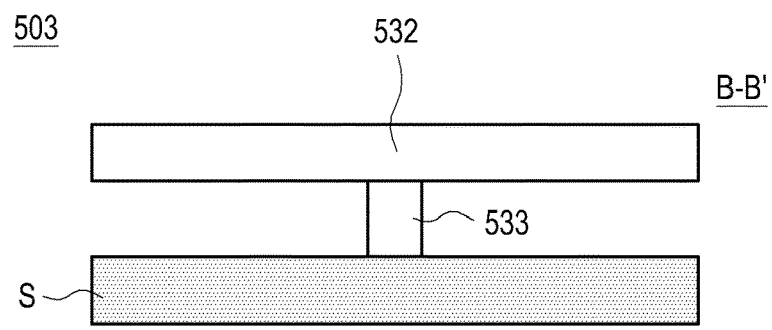
FIG. 20 is a sectional view taken along line B-B' illustrating the collection part of FIG. 17.
Figure 21:
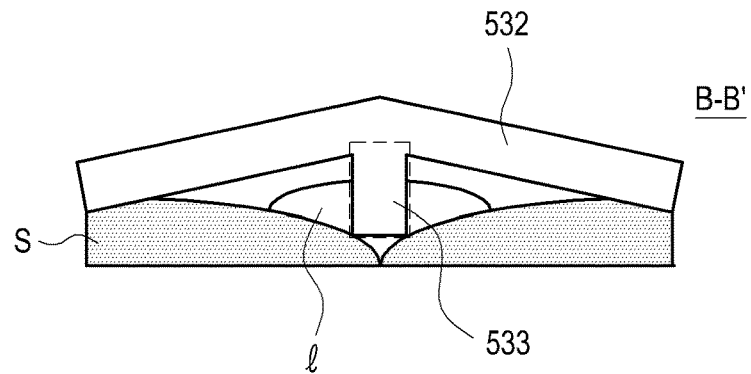
FIG. 21 is a sectional view taken along line B-B' illustrating a state in which the collection part of FIG. 17 is in contact with a skin.

FIG. 17 is a perspective view illustrating the collection part of the wearable body composition analyzer according to yet another one of various embodiments of the present disclosure. FIG. 18 is a sectional view taken along line A-A' illustrating the collection part of FIG. 17. FIG. 19 is a sectional view taken along line A-A' illustrating a state in which the collection part of FIG. 17 is in contact with a skin. FIG. 20 is a sectional view taken along line B-B' illustrating the collection part of FIG. 17. FIG. 21 is a sectional view taken along line B-B' illustrating a state in which the collection part of FIG. 17 is in contact with a skin. A description for components similar to the components of the above-described embodiments from among components of the present embodiment will be omitted, and a collection part will be mainly described. Referring to FIGS. 17 to 21, a collection part 503 may include a space provision part including a cover part 532 and a contact part 531. The contact part 531 may extend from the cover part 532 to be in contact with the skin. The contact part 531 may form a closed curve to form the collection space 535. Further, the space provision part may further include a support part 533 extending from a lower portion of the cover part 532 within a closed curve region constituting the contact part 531.

The support part 533 may prevent a close contact between the cover part 532 and the skin. Further, the support part 533 may prevent the collection part 503 from being reduced together with the contact part 531.

Further, the cover part 532 may be made of a flexible material. As illustrated in FIGS. 19 and 21, when the support part 533 rises towards the upper side of the skin after the support part 533 is in contact with the skin, the cover part 532 made of a flexible material may be bent. Accordingly, the collection space 535 having a predetermined size (e.g., a volume) may be formed and maintained between the cover part 532 and the skin as the contact part 531 is in contact with the support part 533. The bodily liquid 1 may be collected in the collection space 535. Further, the collection part 503 applied to the present embodiment may prevent a communication opening 534 communicating with the movement path part from being blocked by the skin.

Figure 22:
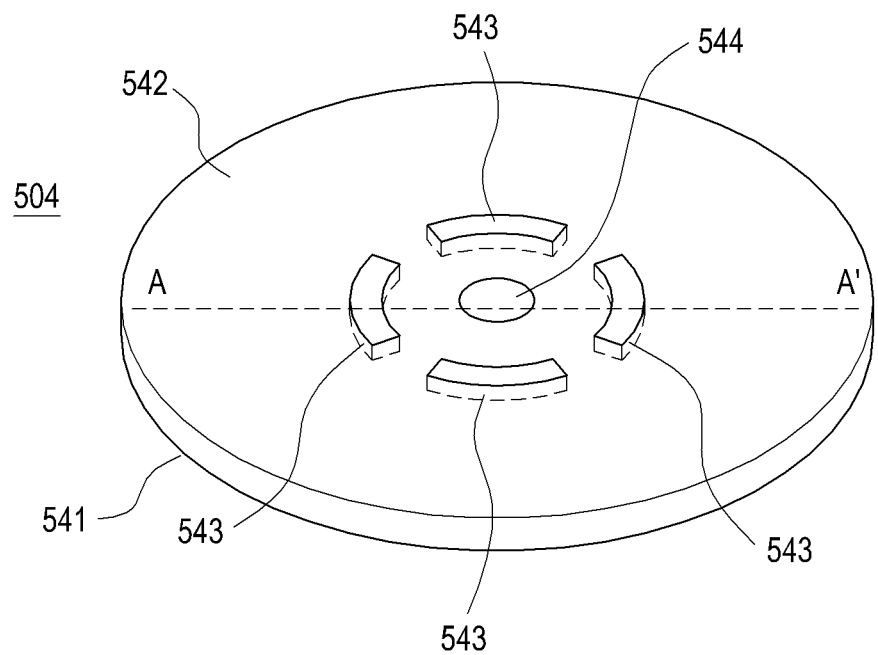
FIG. 22 is a perspective view illustrating a collection part of a wearable body composition analyzer according to yet another one of various embodiments of the present disclosure.
Figure 23:
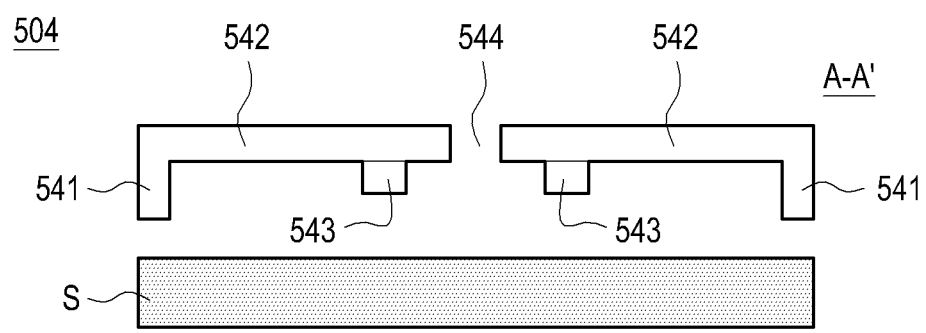
FIG. 23 is a sectional view taken along line A-A' illustrating the collection part of FIG. 22.
Figure 24:
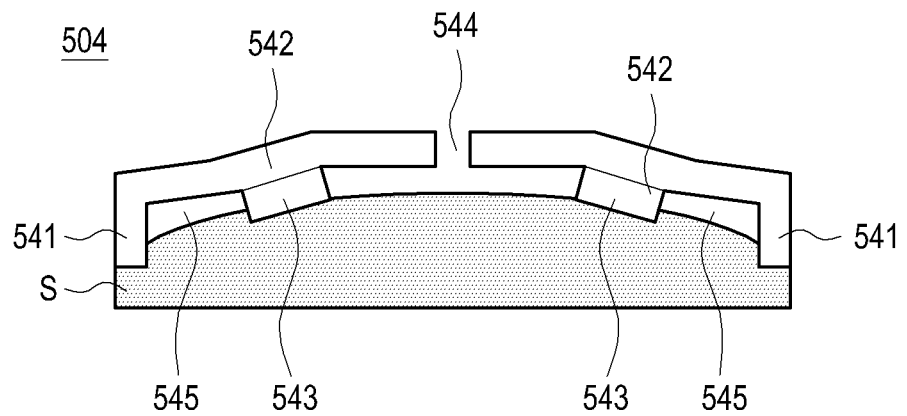
FIG. 24 is a sectional view taken along line A-A' illustrating a state in which the collection part of FIG. 22 is in contact with a skin.

FIG. 22 is a perspective view illustrating a collection part of a wearable body composition analyzer according to yet another one of various embodiments of the present disclosure. FIG. 23 is a sectional view taken along line A-A' illustrating the collection part of FIG. 22. FIG. 24 is a sectional view taken along line A-A' illustrating a state in which the collection part of FIG. 22 is in contact with a skin. A description for components similar to the components of the above-described embodiments from among components of the present embodiment will be omitted, and a collection part will be mainly described.

Referring to FIGS. 22 to 23, a collection part 504 may include a space provision part including a cover part 542, a contact part 541, and a plurality of support parts 543. The contact part 541 may extend from the cover part 542 to be in contact with the skin. The contact part 541 may form a closed curve to form the collection space 545.

The plurality of support parts 543 may be arranged to be spaced apart from each other by a predetermined interval along a circumferential direction of the cover part 542, and may form a space (e.g., the above-described collection space) between the cover part 542 and the skin when being in contact with the skin. A space formed inside the support parts 543 may communicate with the communication opening 544. The communication opening 544 may communicate with the movement path part (not illustrated). As illustrated in FIG. 24, the plurality of support parts 543 may prevent the cover part 542 from being in close contact with the skin. Further, the plurality of support parts 543 prevents the collection space 545 from being reduced by the skin so that the bodily liquid may be collected in the collection space 545. Further, the plurality of support parts 543 may prevent the communication opening 544 from being blocked by the skin.

Figure 25:
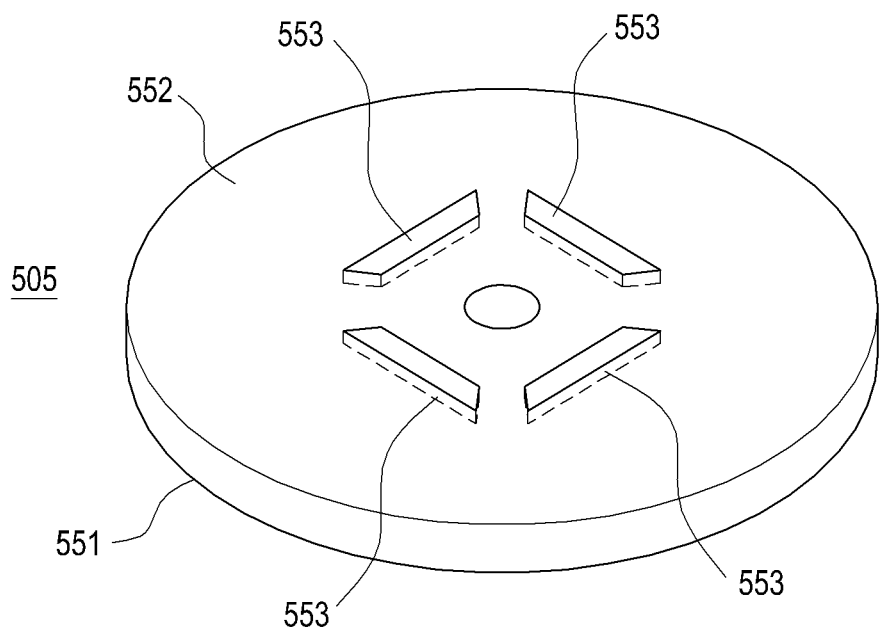
FIG. 25 is a perspective view illustrating a collection part of a wearable body composition analyzer according to yet another one of various embodiments of the present disclosure.

FIG. 25 is a perspective view illustrating a collection part of a wearable body composition analyzer according to yet another one of various embodiments of the present disclosure. Referring to FIG. 25, a collection part 505 may include a space provision part including a cover part 552, a contact part 551, and a plurality of support parts 553. The contact part 551 may extend from the cover part 552 to be in contact with the skin. The contact part 551 may form a closed curve to form the collection space 535.

The plurality of support parts 553 are formed so as to form a rectangular space at a lower portion of the cover part 552. In this way, the support parts may have various structures and shapes which may prevent a close contact between the cover part and the skin.

Figure 26:
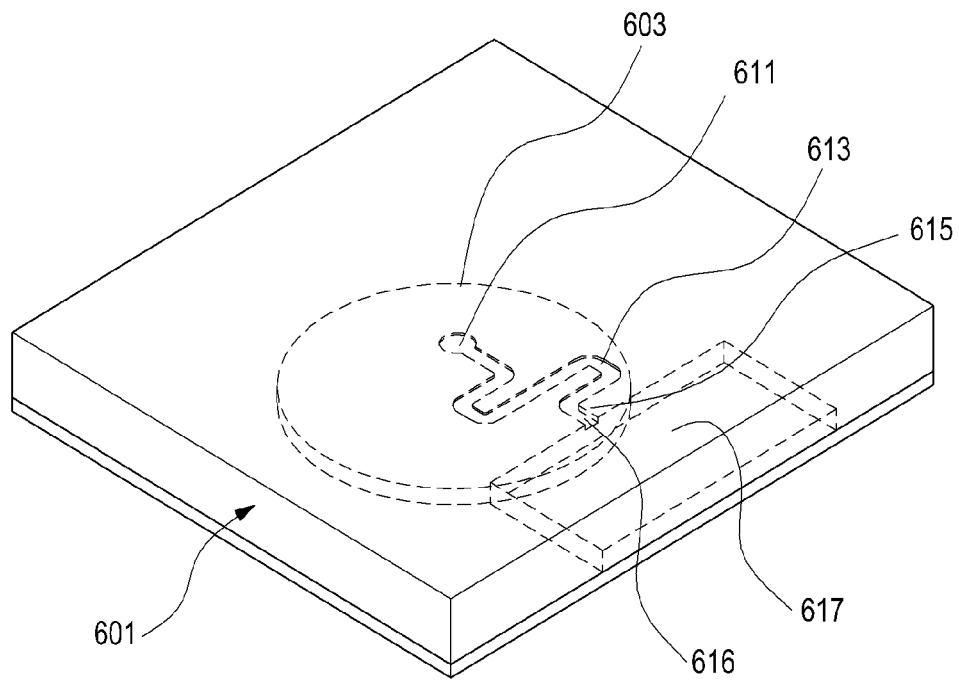
FIGS. 26, 27, and 28 are perspective views illustrating a path in which body fluid is moved within the collection part of the wearable body composition analyzer according to yet another one of various embodiments.
Figure 27:
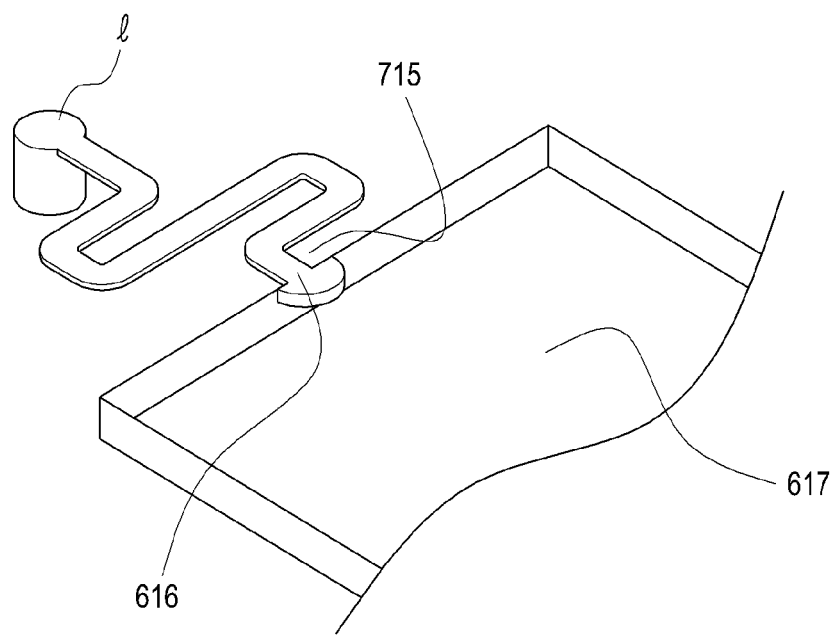
Figure 28:
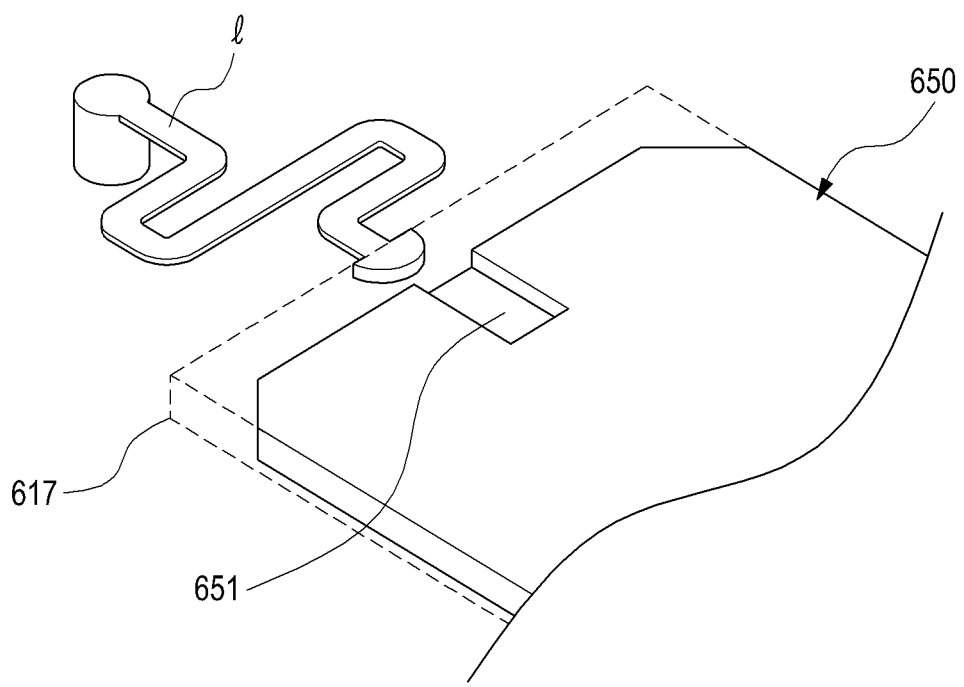

FIGS. 26 to 28 are perspective views illustrating a path in which body fluid is moved within the collection part of the wearable body composition analyzer according to yet another one of various embodiments. Referring to FIGS. 26 to 28, a collection part 601 may include a space provision part 603, a movement path part 613, and a sensor coupling part 617.

The collection part 601 may collect bodily liquid secreted from the skin. For example, a collection space according to the above-described embodiment may be formed inside the space provision part 603. The space provision part 603 may have a communication opening 611 (e.g., the above-described communication opening) communicating with the movement path part 613. The bodily liquid 1 may move to the movement path part 613 by a capillary phenomenon through the communication opening 611. The sensor coupling part 617 is connected to the movement path part 613 and may provide a space into which the sensor part is inserted. Further, the movement path part 613 may have a length longer than the shortest distance to the sensor coupling part 617. That is, the movement path part 613 may be formed in a zigzag form. Further, as illustrated in FIG. 27, the bodily liquid 1 is exposed to the outside through a discharge opening 616 formed at an end of the movement path part 613 so as to be discharged in a bubble shape. For example, the bodily liquid 1 having moved along the movement path part 613 may be formed in a bubble shape before being discharged to the outside of the movement path part 613. Further, when a sensor part 650 is coupled to the sensor coupling part 617, the bodily liquid 1 of a bubble shape may come into contact with a bodily liquid contact part 651 of the sensor part 650. Accordingly, the sensor part 650 may detect a body composition from the bodily liquid.

Figure 29:
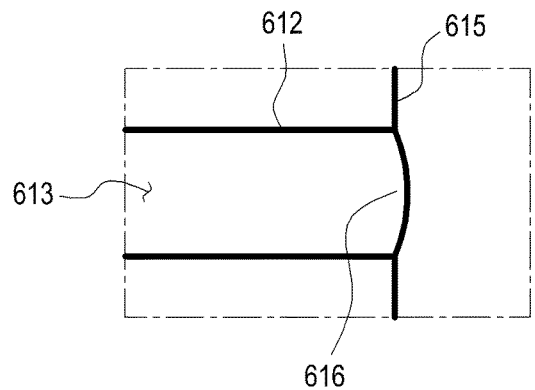
FIGS. 29, 30, and 31 are views for describing a process of stopping body fluid at one end of a movement path part of the wearable body composition analyzer according to yet another one of various embodiments of the present disclosure.
Figure 30:
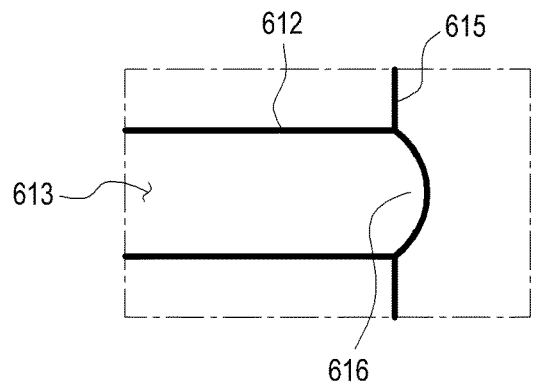
Figure 31:
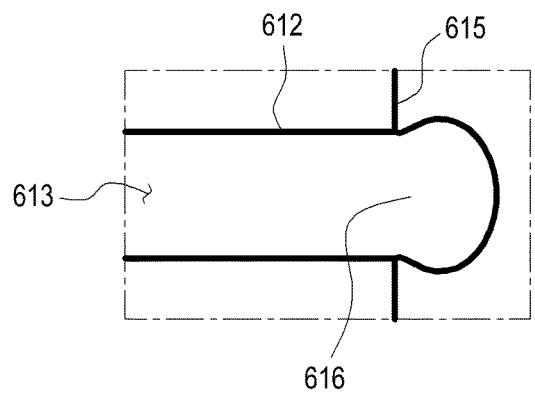

FIGS. 29 to 31 are sectional views illustrating a process of stopping body fluid at one end of a moving path part of the wearable body composition analyzer according to yet another one of various embodiments of the present disclosure. The movement path part 613 according to various embodiments of the present disclosure may be made of a hydrophil material. Further, one end 615 of the movement path part 613 may be made of a hydrophobic material. As illustrated in FIG. 29, the bodily liquid 1 having passed through the movement path part 613 may move to the discharge opening 616. Further, as illustrated in FIG. 30, the bodily liquid 1 may stop at the discharge opening 616 by the movement path part 613 and the one end 615 of the movement path part without being discharged through the discharge opening 616. Further, as illustrated in FIG. 31, the bodily liquid 1 may be formed in a bubble shape at the discharge opening 616. That is, the bodily liquid 1 flowing along the movement path part 613 by the capillary phenomenon may be formed in a bubble shape without spreading as a surface state thereof is changed to a hydrophobic property at the discharge opening 616. Further, the bodily liquid 1 may be formed in a bubble shape by the surface tension while being discharged to the outside of the discharge opening 616. That is, although an outer space of the discharge opening 616 is increased as compared with the movement path part 613, the one end 615 of the movement path part is made of a hydrophobic material so that the bodily liquid may be maintained in a bubble shape by the surface tension while being exposed to the outside of the discharge opening 616.

In this way, the movement path part 613 according to various embodiments of the present disclosure is made of a hydrophil material and the one end 615 of the movement path part is made of a hydrophobic material, so that the bodily liquid 1 may stop at the discharge opening 616 without a separate valve apparatus.

Figure 32:
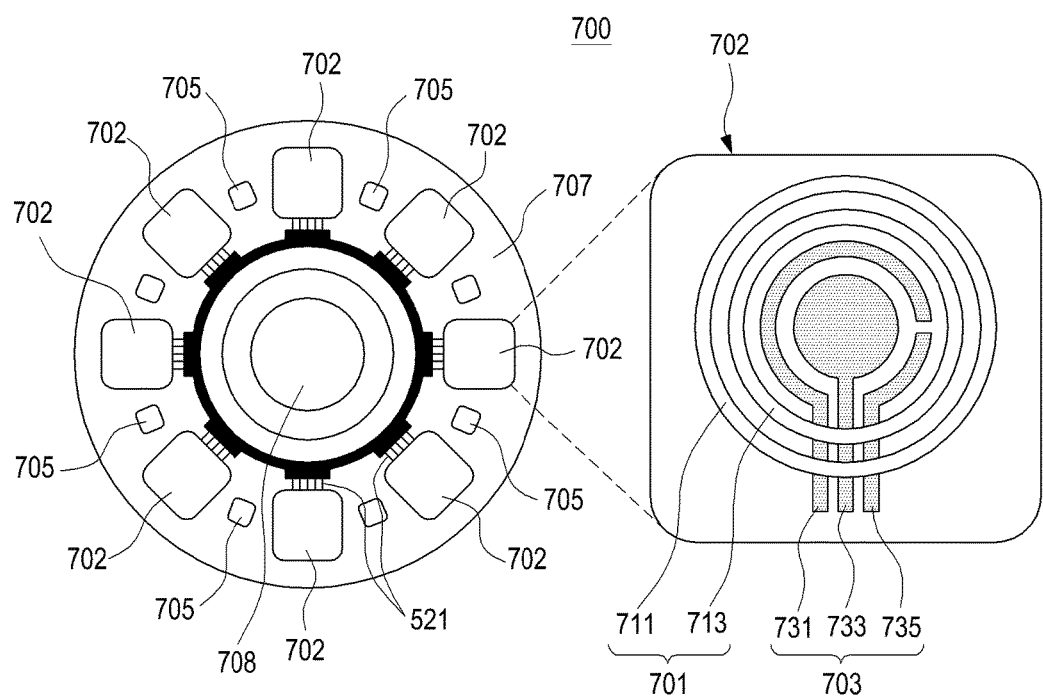
FIG. 32 is a view schematically illustrating the wearable body composition analyzer according to yet another one of various embodiments of the present disclosure.
Figure 33:
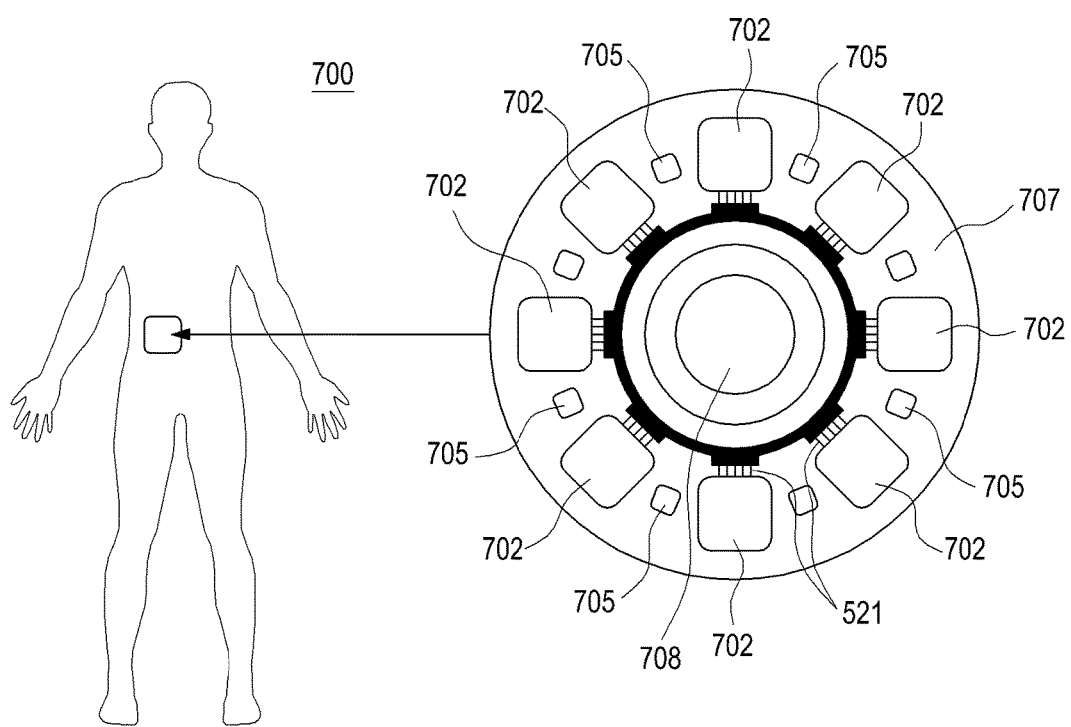
FIG. 33 is a view illustrating a state in which the wearable body composition analyzer is attached to a body according to yet another one of various embodiments of the present disclosure.

FIG. 32 is a view schematically illustrating the wearable body composition analyzer according to yet another one of various embodiments of the present disclosure. FIG. 33 is a view illustrating a state in which the wearable body composition analyzer is attached to a body according to yet another one of various embodiments of the present disclosure.

Referring to FIGS. 32 to 33, a wearable body composition analyzer 700 according to yet another one of various embodiments of the present disclosure may include a wearable part 707, a driving circuit part 708, an induction part 701, a sensor part 703, and one or more attachment parts 702.

The wearable part 707 may be worn on a part of the body. The wearable part 707 according to the present embodiment may be a patch type. A part of the wearable part 707 in contact with the body may be made of a material having an adhesive force. Accordingly, a user may attach the wearable part 707 to a body covered by clothes. The driving circuit part 708 may be arranged at the center of the wearable part 707. The induction part 701 may include a first induction part 711 and a second induction part 713, and the sensor part 703 may include an operation electrode 731, a counter electrode 733, and an auxiliary electrode 735.

The attachment part 702 may include the induction part 701 and the sensor part 703. The induction part 701 and the sensor part 703 may be integrally attached to the attachment part 702. Further, the induction part 701 may protrude from one surface of the attachment part 702. The first induction part 711 may be arranged to be spaced apart from the circumference of the sensor part 703, and the second induction part 713 may protrude from one surface of the attachment part 702 and be arranged between the first induction part 711 and the sensor part 703. A plurality of attachment parts 702 each including the induction part 701 and the sensor part 703 may be formed. The plurality of attachment parts 702 may be arranged at the circumference of the driving circuit part 708 along the circumferential direction of the wearable part. Further, the induction part 701 and the sensor part 703 included in the attachment part 702 may be electrically connected to the driving circuit part 708.

Further, the wearable body composition analyzer according to the present embodiment may further include a washing part 705.

The washing part 705 is mounted to the wearable part 707, and may spray washing liquid to a part where the attachment part 702 is in contact with the skin. The washing part 705 may be arranged between the plurality of attachment parts 702, but is not limited thereto.

In this way, in the wearable body composition analyzer according to various embodiments of the present disclosure, the plurality of attachment part 702 each including the induction part 701 and the sensor part 703 are formed so that a user wears the wearable body composition analyzer 700 one time and then repeatedly analyzes a body composition times of the number of the attachment parts 702. According to various embodiments, the wearable body composition analyzer 700 may be used to analyze a body composition repeatedly by the number of the attachment parts 702. However, when one attachment part analyzes a body composition and then analyzes a body composition again, the accuracy of the analysis performed later may be reduced due to a body composition remaining in the attachment part 702 by the firstly-performed analysis. Therefore, when one attachment part repeatedly analyzes a body composition using the washing part 705, the interior of the corresponding attachment part may be washed.

Figure 34:
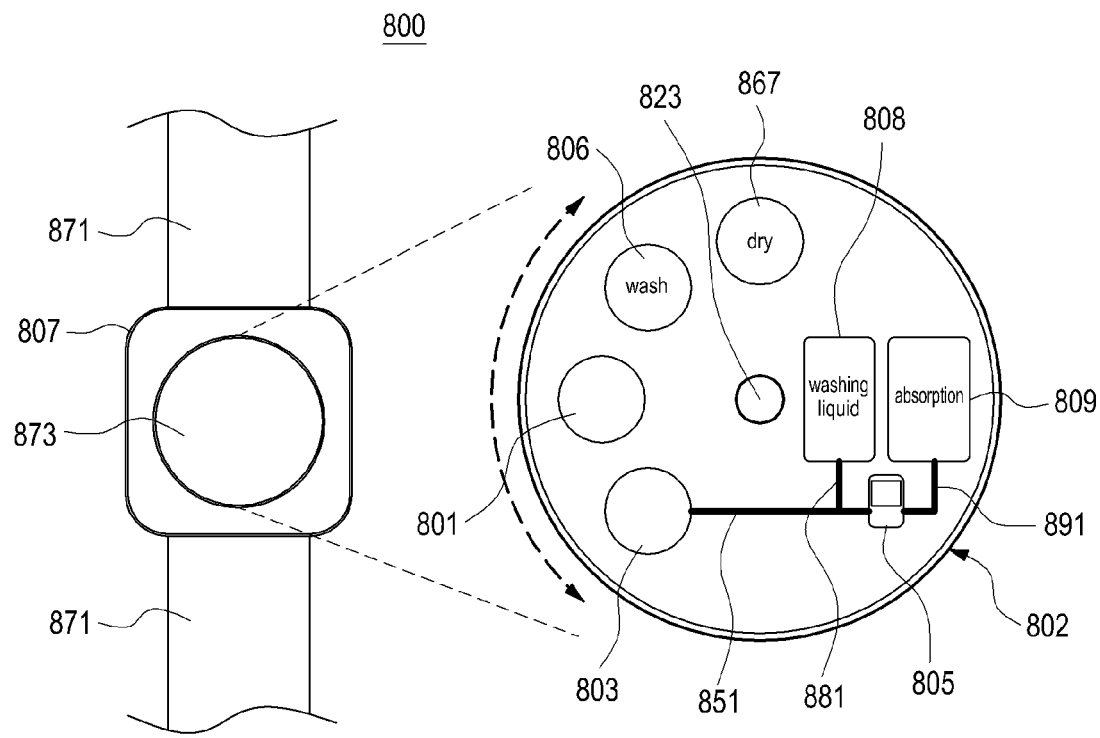
FIG. 34 is a plan view illustrating the wearable body composition analyzer according to yet another one of various embodiments of the present disclosure.
Figure 35:
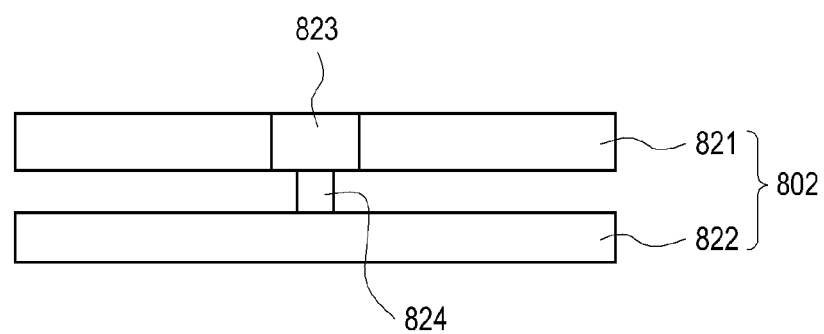
FIG. 35 is a sectional view illustrating a body part of FIG. 34.

FIG. 34 is a plan view illustrating the wearable body composition analyzer according to yet another one of various embodiments of the present disclosure. FIG. 35 is a sectional view illustrating a body part of FIG. 34. Referring to FIGS. 34 to 35, a wearable body composition analyzer 800 according to yet another one of various embodiments of the present disclosure may include a wearable part 807, a body part 802, an induction part 801, a collection part 803, and a sensor part 805.

The wearable part 807 may be worn on a part of the body. The wearable part 807 may be a watch type or a band type. The wearable part 807 may include a band part 871 worn on the body, e.g., a wrist of the user. However, the wearable part 807 is not limited to a watch type or a band type, and may have various types which may be worn on the body.

The body part 802 may be attached to the wearable part 807. The body part 802 may rotate on the wearable part 807. The body part 802 may include a first body part 821 and a second body part 822. The first body part 821 may include a driving part 823 attached and fixed to the wearable part 807 to provide a rotation force. For example, the driving part 823 may provide a rotation force to a rotary shaft 824 connected to the driving part 823. The second body part 822 may be connected to the rotary shaft 824 and may be rotated by the driving part 823.

The induction part 801 is mounted to the second body part 822 and may induce a secretion of the bodily liquid while being in contact with the skin. The collection part 803 is mounted to the second body part 822 and may induce a secretion of the bodily liquid while being in contact with the skin. The sensor part 805 may be mounted to the second body part 882 and detect a body composition from bodily liquid collected by the collection part 803.

A process of operating the wearable body composition analyzer 800 will be described below. First, the body part 802 is rotated after an inductive agent is injected by the induction part 801, so that the collection part 803 may be arranged at a location where the induction part 801 is in contact with the skin. For example, when a predetermined time (e.g., tens of seconds to several minutes) is elapsed after the inductive agent is injected, bodily liquid is secreted through the skin. At this time, the body part may arrange the collection part 803 at a location where the induction part 801 is located before the bodily liquid is secreted. Further, the collection part 803 may transfer the bodily liquid to the sensor part 805 after collecting the bodily liquid secreted from the skin. The sensor part 805 may detect a body composition from the bodily liquid.

Further, the wearable body composition analyzer 800 according to yet another one of the present disclosure may further include a washing pad part 806 and a drying pad part 867.

The washing pad part 806 may be mounted to the body part 802 and may wash the skin of a body. The washing pad part 806 may wash a part where the induction part 801 is in contact with the skin of a body before/after the induction part 801 is operated.

The drying pad part 867 may be mounted to the second body part 882 and may dry the skin of a body. After the washing pad part 806 washes the skin of a body, the drying pad part 867 may rotate the second body part 882 to locate the second body part 882 at the skin washed by the washing pad part 806. The drying pad part 867 may dry fluid such as water when the fluid exists on the skin before the induction part 801 is not used.

Further, the induction part 810, the collection part 803, the washing pad part 806, and the drying pad part 867 may be arranged within the same radius from the center of the second body part 822. Accordingly, when the second body part 822 is rotated, the induction part 810, the collection part 803, the washing pad part 806, and the drying pad part 867 may be in contact with the skin at the same location.

Further, the wearable body composition analyzer 800 according to yet another one of the present disclosure may further include an introduction line 851, a washing liquid supply part 808, a discharge line 891, and an absorption part 809.

The introduction line 851 may connect the collection part 803 to the sensor part 805. The bodily liquid collected by the collection part 803 may move the sensor part 805 along the introduction line 851. The washing liquid supply part 808 may be connected to the introduction line 851 and inject washing liquid through the introduction line 851. The discharge line 891 may be connected to the sensor part 805 and may discharge the washing liquid or the bodily liquid. The absorption part 809 may absorb the washing liquid or the bodily liquid discharged through the discharge line 891. As the introduction line 851, the washing liquid supply part 808, the discharge line 891, and the absorption part 809 are connected to the sensor part 805, the bodily liquid of the sensor part 805 is washed so that the sensor part 805 may be repeatedly used.

Figure 36:
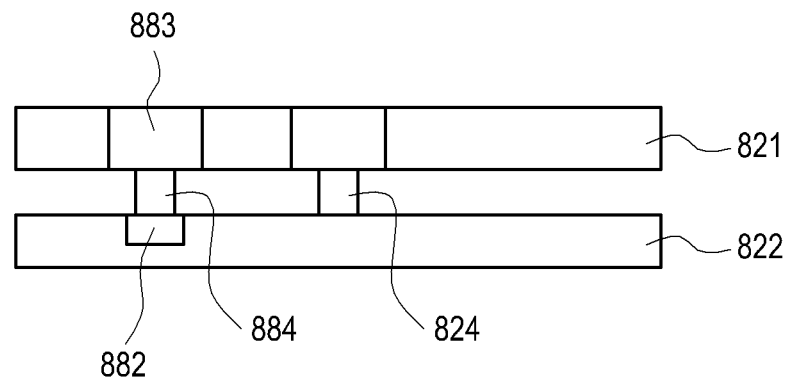
FIG. 36 is a sectional view illustrating a body part and a washing liquid supply part applied to the wearable body composition analyzer according to yet another one of various embodiments of the present disclosure.
Figure 37:
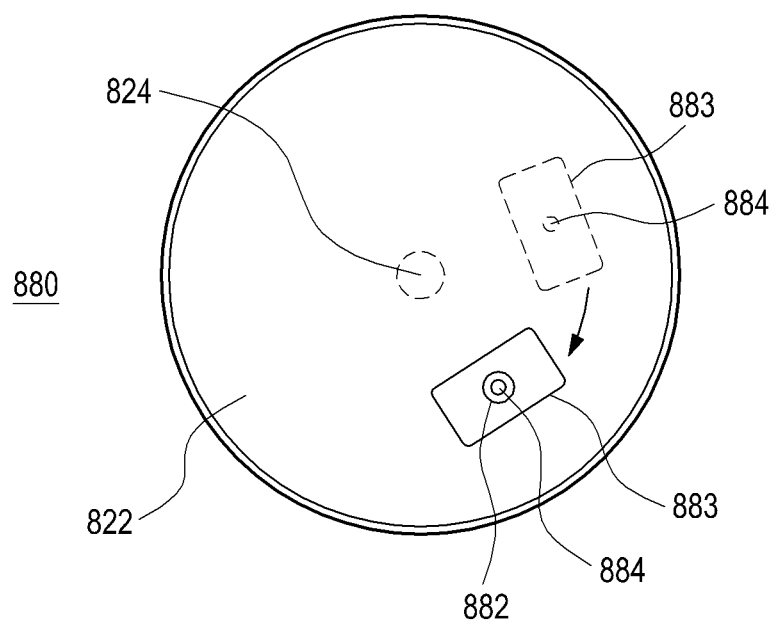
FIG. 37 is a view illustrating a state in which the washing liquid supply part of FIG. 36 is connected to a washing line according to rotation.

FIG. 36 is a sectional view illustrating a body part and a washing liquid supply part applied to the wearable body composition analyzer according to yet another one of various embodiments of the present disclosure. FIG. 37 is a view illustrating a state in which the washing liquid supply part of FIG. 36 is connected to a washing line according to rotation.

Referring to FIGS. 36 and 37, a washing liquid supply part 883 applied to a wearable body composition analyzer 880 according to yet another one of various embodiments of the present disclosure may be formed in the first body part 821, and the introduction line 851 (FIG. 34) may be formed in the second body part 822.

The washing liquid supply part 883 may include a pipe 884 communicating with the washing liquid supply part 883. The pipe 884 may have a length corresponding to a distance between the first body part 821 and the second body part 822 (FIG. 34). The introduction line 851 (FIG. 34) may have a connection opening communicating with the pipe 884. As illustrated in FIG. 37, the pipe 884 may communicate with the connection opening by the rotation of the second body part 822. Thus, as the washing liquid supply part 883 is not formed in the first body part 821 not rotated, energy necessary for rotating the second body part 822 may be saved as compared with a case where the washing liquid supply part is formed in the second body part 822.

Figure 38:
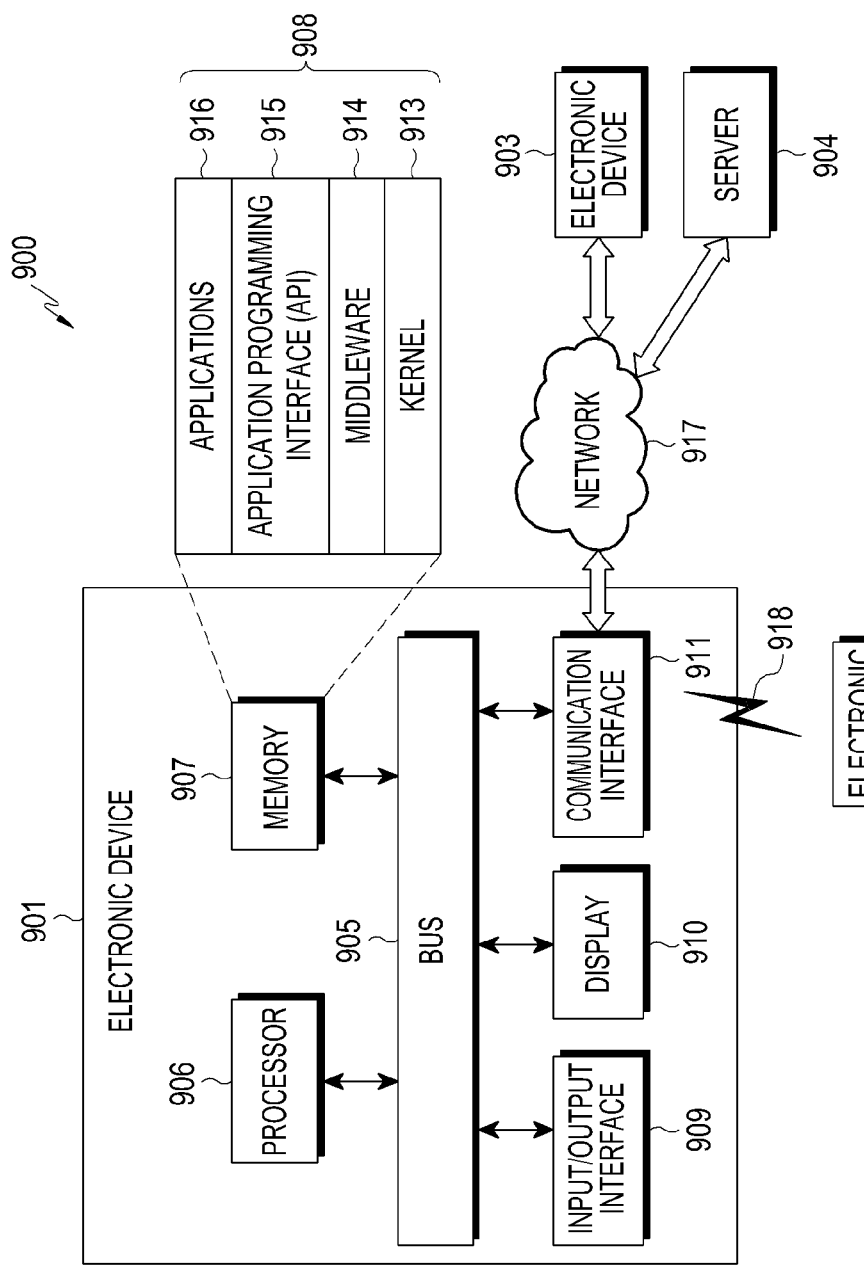
FIG. 38 is a view illustrating a network environment in which the wearable body composition analyzer operates according to various embodiments of the present disclosure.

FIG. 38 is a view illustrating a network environment in which the wearable body composition analyzer operates according to various embodiments of the present disclosure.

A wearable body composition analyzer according to various embodiments of the present disclosure may be one of electronic devices. A wearable body composition analyzer according to various embodiments of the present disclosure may interwork with various electronic devices.

For example, the electronic device may include at least one of a smartphone, a tablet personal computer (PC), a mobile phone, a video phone, an electronic book (e-book) reader, a desktop PC, a laptop PC, a netbook computer, a personal digital assistant (PDA), a portable multimedia player (PMP), an MP3 player, a mobile medical appliance, a camera, and a wearable device (e.g., a head-mounted-device (HMD) such as electronic glasses, electronic clothes, an electronic bracelet, an electronic necklace, an electronic appcessory, electronic tattoos, or a smart watch).

According to some embodiments, the electronic device may be a smart home appliance. The home appliance may include at least one of, for example, a television, a Digital Video Disk (DVD) player, an audio, a refrigerator, an air conditioner, a vacuum cleaner, an oven, a microwave oven, a washing machine, an air cleaner, a set-top box, a home automation control panel, a security control panel, a TV box (e.g., Samsung HomeSync™, Apple TV™, or Google TV™), a game console (e.g., Xbox™ and PlayStation™), an electronic dictionary, an electronic key, a camcorder, and an electronic photo frame.

According to another embodiment, the electronic device may include at least one of various medical devices (e.g., various portable medical measuring devices (a blood glucose monitoring device, a heart rate monitoring device, a blood pressure measuring device, a body temperature measuring device, etc.), a Magnetic Resonance Angiography (MRA), a Magnetic Resonance Imaging (MRI), a Computed Tomography (CT) machine, and an ultrasonic machine), a navigation device, a Global Positioning System (GPS) receiver, an Event Data Recorder (EDR), a Flight Data Recorder (FDR), a Vehicle Infotainment Devices, an electronic devices for a ship (e.g., a navigation device for a ship, and a gyro-compass), avionics, security devices, an automotive head unit, a robot for home or industry, an automatic teller's machine (ATM) in banks, point of sales (POS) in a shop, or internet device of things (e.g., a light bulb, various sensors, electric or gas meter, a sprinkler device, a fire alarm, a thermostat, a streetlamp, a toaster, a sporting goods, a hot water tank, a heater, a boiler, etc.).

According to some embodiments, the electronic device may include at least one of a part of furniture or a building/structure, an electronic board, an electronic signature receiving device, a projector, and various kinds of measuring instruments (e.g., a water meter, an electric meter, a gas meter, and a radio wave meter). In various embodiments, the electronic device may be a combination of one or more of the aforementioned various devices. The electronic device according to some embodiments of the present disclosure may be a flexible device. Further, the electronic device according to an embodiment of the present disclosure is not limited to the aforementioned devices, and may include a new electronic device according to the development of technology.

Hereinafter, with reference to the accompanying drawings, a wearable body composition analyzer according to various embodiments of the present disclosure will described while being called an electronic device. As used herein, the term "user" may indicate a person who uses an electronic device or a device (e.g., an artificial intelligence electronic device) that uses an electronic device.

An electronic device 901 within a network environment 900 according to various embodiments will be described with reference to FIG. 38. The electronic device 901 may include a bus 905, a processor 906, a memory 907, an input/output interface 909, a display 910, and a communication interface 911. In any embodiment, the electronic device 901 may omit at least one of the above components or further include other components.

The bus 905 may connect the processor 906 to the memory 907, the input/output interface 909, the display 910, and the communication interface 911, and to transfer communication (e.g., a control message and/or data) between the processor 906, the memory 907, the input/output interface 909, the display 910, and the communication interface 911.

The processor 906 may include one or more of a Central Processing Unit (CPU), an Application Processor (AP), and a Communication Processor (CP). The processor 906 can, for example, control one or more other components of the electronic device 901 and/or process an operation or data related to communication.

The memory 907 may include a volatile memory and/or a non-volatile memory. The memory 907 may store, for example, instructions or data related to at least one other component of the electronic device 901. According to an embodiment, the memory 907 may store software and/or a program 908. The program 908 may include, for example, a kernel 913, a middleware 914, an Application Programming Interface (API) 915, and/or applications 916. At least some of the kernel 913, the middleware 914, and the API 915 may be referred to as an Operating System (OS).

For example, the kernel 913 may control or manage system resources (e.g., the bus 905, the processor 906, and the memory 907) used to execute an operation or a function implemented in the other programs (e.g., the middleware 914, the API 915, and the applications 916). Further, the kernel 913 may provide an interface through which the middleware 914, the API 915, or the applications 916 may access individual components of the electronic device 901 to control or manage system resources.

For example, the middleware 914 may serve as a relay for allowing the API 915 or the applications 916 to communicate with the kernel 913 to exchange data. Further, in regard to task requests received from the applications 916, the middleware 914 may make a control (e.g., scheduling or load balancing) for the task requests using, for example, a method of assigning at least one application a priority for using the system resources (e.g., the bus 905, the processor 906, or the memory 907) of the electronic device 901.

The API 915 is an interface by which the applications 916 control functions provided from the kernel 913 or the middleware 914, and may include, for example, at least one interface or function (e.g., instructions) for file control, window control, image processing, or text control.

The input/output interface 909 may serve as an interface which may transmit commands or data input from a user or another external device to other component(s) of the electronic device 901. Further, the input/output interface 909 may output instructions or data received from another component(s) of the electronic device 901 to a user or another external device.

The display 910 may include, for example, a Liquid Crystal Display (LCD), a Light Emitting Diode (LED) display, an Organic Light Emitting Diode (OLED) display, a Micro Electro Mechanical System (MEMS) display, or an electronic paper display. The display 910 may display various types of contents (e.g., text, images, videos, icons, or symbols) for users. The display 910 may include a touch screen and receive, for example, a touch input, a gesture input, a proximity input, or a hovering input using an electronic pen or a user's body part. Further, the display 910 may display a level of a body composition (e.g., blood sugar) detected from bodily liquid.

For example, the communication interface 911 may set communication between the electronic device 901 and a first electronic device 902, a second electronic device 903, or a server 904. For example, the communication interface 911 may be connected to a network 917 through wireless or wired communication to communicate with the external device (e.g., the second electronic device 903 or the server 904) so as to transmit information on the detected body composition to the external electronic device (e.g., the second electronic device 903 or the server 904).

The wireless communication may use at least one of, for example, LTE, LTE-A, Code division multiple access (CDMA), Wide Code division multiple access (WCDMA), Universal Mobile Telecommunications System (UMTS), Wireless Broadband (WiBro), and Global System for Mobile (GSM) as a cellular communication protocol. The wired communication may include, for example, at least one of a Universal Serial Bus (USB), a High Definition Multimedia Interface (HDMI), Recommended Standard 232 (RS-232), and a Plain Old Telephone Service (POTS). The network 917 may include at least one of communication networks such as a computer network (e.g., a local area network (LAN) or a wide area network (WAN)), the Internet, and a telephone network.

Each of the first electronic device 902 and the second electronic device 903 may be a device which is the same as or different from the electronic device 901. According to an embodiment, the server 904 may include a group of one or more servers.

According to various embodiments, all or some of the operations performed in the electronic device 901 may be executed by another electronic device or a plurality of electronic devices (e.g., the first electronic device 902, the second electronic device 903, or the server 904). According to an embodiment, when the electronic device 901 should perform some functions or services automatically or by request, the electronic device 901 may make a request for performing at least some of the functions related to the functions or services to another device (e.g., the first electronic device 902, the second electronic device 903, or the server 904) instead of performing the functions or services by itself. The first electronic device 902, the second electronic device 903 or the server 904, for example, may execute the requested function or the additional function and transfer the result, obtained by executing the function, to the electronic device 901. The electronic device 901 may provide the requested functions or services based on the received result as it is or after additionally processing the received result. To achieve this, for example, cloud computing, distributed computing, or client-server computing technology may be used.

Figure 39:
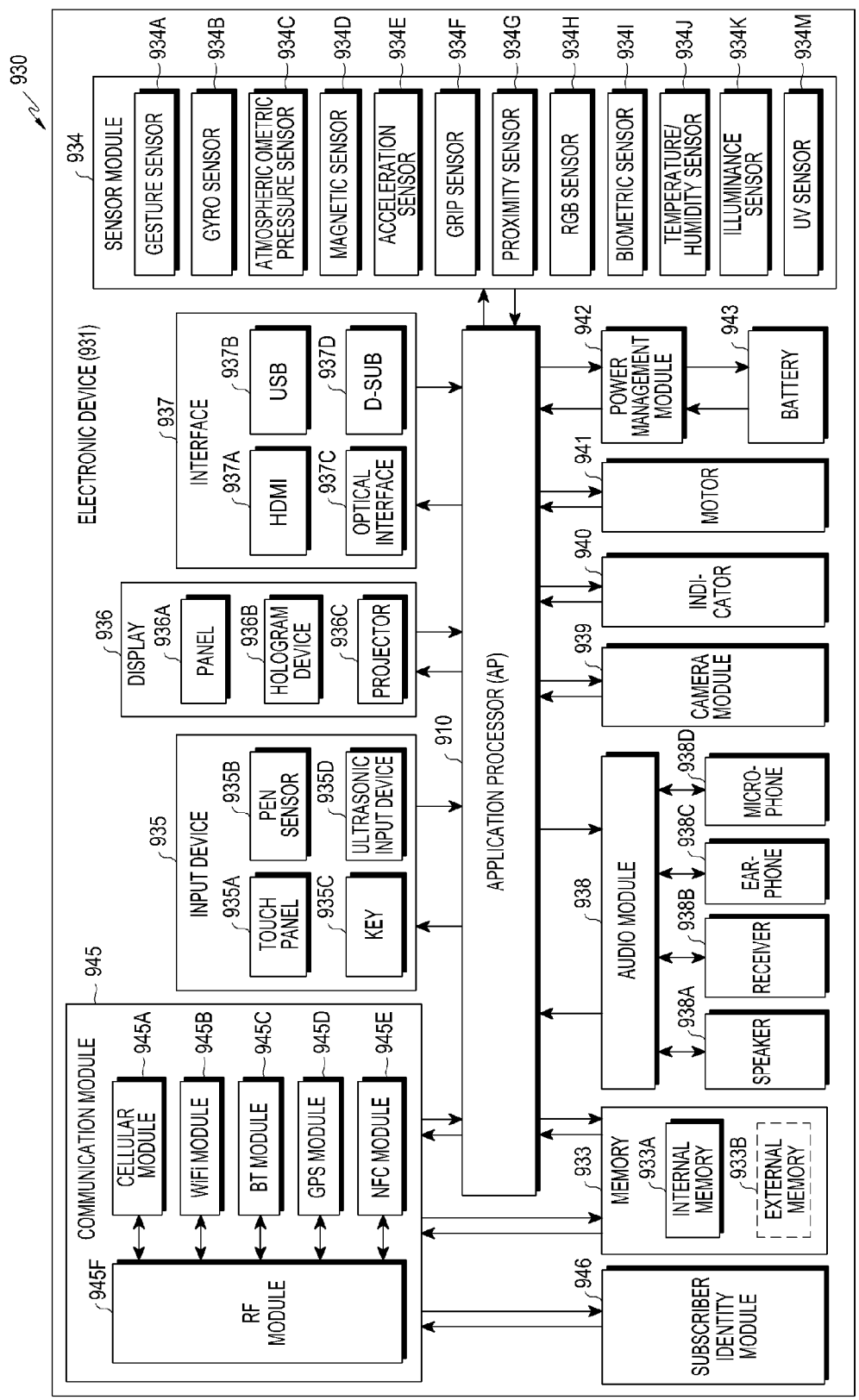
FIG. 39 is a block diagram illustrating an electronic device according to various embodiments of the present disclosure.

FIG. 39 is a block diagram 930 illustrating an electronic device 931 according to various embodiments of the present disclosure. The electronic device 931 may include, for example, all or some of the electronic device 901 illustrated in FIG. 38. The electronic device 931 may include an Application Processor (AP) 932, a communication module 945, a Subscriber Identification Module (SIM) card 946, a memory 933, a sensor module 934, an input device 935, a display 936, an interface 937, an audio module 938, a camera module 939, a power management module 942, a battery 943, an indicator 940, and a motor 941.

The AP 932 may control a plurality of hardware or software components connected thereto by driving an operating system or an application program and perform a variety of data processing and calculations. Further, the AP 932 may calculate a numerical level of the body composition from the detected bodily liquid. The AP 932 may be embodied as, for example, a System on Chip (SoC). According to an embodiment, the AP 932 may further include a Graphical Processing Unit (GPU) and/or an image signal processor. The AP 932 may also include at least some (e.g., a cellular module 945A) of the components illustrated in FIG. 39. The AP 932 may load instructions or data, received from at least one other component (e.g., a non-volatile memory), in a volatile memory to process the loaded instructions or data, and may store various types of data in a non-volatile memory. The communication module 945 may have a configuration equal or similar to the communication interface 911 of FIG. 38. The communication module 945 may include, for example, a cellular module 945A, a Wi-Fi module 945B, a Bluetooth (BT) module 945C, a global positioning system (GPS) module 945D, a Near field communication (NFC) module 945E, and a Radio Frequency (RF) module 945F.

The cellular module 945A may provide a voice call, video call, text message services, or Internet services through, for example, a communication network. According to an embodiment, the cellular module 945A may distinguish between and authenticate electronic devices, such as, for example, the electronic device 931, within a communication network using a subscriber identification module (e.g., the SIM card 946). According to an embodiment, the cellular module 945A may perform at least some of the functions which may be provided by the AP 932. According to an embodiment, the cellular module 945A may include a Communication Processor (CP).

Each of the Wi-Fi module 945B, the BT module 945C, the GPS module 945D, or the NFC module 945E may include, for example, a processor for processing data transmitted/received through the corresponding modules. According to any embodiment, at least some (two or more) of the cellular module 945A, the Wi-Fi module 945B, the BT module 945C, the GPS module 945D, and the NFC module 945E may be included in one Integrated Chip (IC) or IC package.

The RF module 945F may transmit/receive, for example, a communication signal (e.g., an RF signal). The RF module 945F may include, for example, a transceiver, a Power Amp Module (PAM), a frequency filter, a Low Noise Amplifier (LNA) or an antenna. According to another embodiment, at least one of the cellular module 945A, the Wi-Fi module 945B, the BT module 945C, the GPS module 945D, and the NFC module 945E may transmit/receive an RF signal through a separate RF module.

The SIM card 946 may include a card including a subscriber identification module and/or an embedded SIM, and contain unique identification information (e.g., an Integrated Circuit Card Identifier (ICCID)) or subscriber information (e.g., an International Mobile Subscriber Identity (IMSI)).

The memory 933 may include, for example, an internal memory 933A and an external memory 933B. The internal memory 933A may include at least one of, for example, a volatile memory (e.g., a Dynamic Random Access Memory (DRAM), a Static Random Access Memory (SRAM), a Synchronous Dynamic Random Access Memory (SDRAM), and the like) and a non-volatile memory (e.g., a One Time Programmable Read Only Memory (OTPROM), a Programmable Read Only Memory (PROM), an Erasable and Programmable Read Only Memory (EPROM), an Electrically Erasable and Programmable Read Only Memory (EEPROM), a flash memory (e.g., a NOT AND (NAND) flash memory or a NOT OR (NOR) flash memory), a hard driver, or a Solid State Drive (SSD). The external memory 933B may store a numerical level of a body composition.

The external memory 933B may further include a flash drive, for example, a Compact Flash (CF), a Secure Digital (SD), a Micro Secure Digital (Micro-SD), a Mini Secure Digital (Mini-SD), an extreme Digital (xD), a memory stick, or the like. The external memory 933B may be functionally and/or physically connected to the electronic device 931 through various interfaces.

The sensor module 934 may measure, for example, a physical quantity or detect an operation state of the electronic device 931, and may convert the measured or detected information to an electrical signal. The sensor module 934 may include, for example, at least one of a gesture sensor 934A, a gyro sensor 934B, an atmospheric pressure sensor 934C, a magnetic sensor 934D, an acceleration sensor 934E, a grip sensor 934F, a proximity sensor 934G, a color sensor 934H (e.g., red, green, and blue (RGB) sensor), a biometric sensor 934I, a temperature/humidity sensor 934J, an illumination sensor 934K, and an Ultra Violet (UV) sensor 934M. Additionally or alternatively, the sensor module 934 may include an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 934 may further include a control circuit for controlling at least one sensor included therein. The biometric sensor 934I may detect a body composition (e.g., blood sugar) from the collected bodily liquid. In any embodiment, the electronic device 931 may further include a processor configured to control the sensor module 934 as a part of or separately from the AP 932, and may control the sensor module 934 while the AP 932 is in a sleep state. Further, in a case where a plurality of sensor parts are provided in the above embodiment, when one sensor is operated from among the plurality of sensor parts, the remaining sensor parts may be in a sleep state by the processor.

The input device 935 may include, for example, a touch panel 935A, a (digital) pen sensor 935B, a key 935C, or an ultrasonic input device 935D. The touch panel 935A may use at least one of, for example, a capacitive type, a resistive type, an infrared type, and an ultrasonic type. The touch panel 935A may further include a control circuit. The touch panel 935A may further include a tactile layer, and provide a tactile reaction to a user.

The (digital) pen sensor 935B may include, for example, a recognition sheet which is a part of the touch panel or a separate recognition sheet. The key 935C may include, for example, a physical button, an optical key or a keypad. The ultrasonic input device 935D may input data through an input means that generates an ultrasonic signal, and the electronic device 931 may identify data by detecting a sound wave with a microphone (e.g., a microphone 938D).

The display 936 (e.g., the display 910) may include a panel 936A, a hologram device 936B, or a projector 936C. The panel 936A may include a component equal or similar to the display 910 of FIG. 38. The panel 936A may be implemented to be, for example, flexible, transparent, or wearable. The panel 936A may also be configured to be integrated with the touch panel 935A as a single module. The hologram device 936B may show a stereoscopic image in the air by using interference of light. The projector 936C may project light onto a screen to display an image. For example, the screen may be located inside or outside the electronic device 931. According to an embodiment, the display 936 may further include a control circuit for controlling the panel 936A, the hologram device 936B, or the projector 936C.

The interface 937 may include, for example, a High-Definition Multimedia Interface (HDMI) 937A, a Universal Serial Bus (USB) 937B, an optical interface 937C, or a D-subminiature (D-sub) 937D. The interface 937 may be included in, for example, the communication interface 911 illustrated in FIG. 38. Additionally or alternatively, the interface 937 may include, for example, a Mobile High-definition Link (MHL) interface, a Secure Digital (SD)

card/Multi-Media Card (MMC) interface, or an Infrared Data Association (IrDA) standard interface.

The audio module 938 may bilaterally convert, for example, a sound and an electrical signal. At least some components of the audio module 938 may be included in, for example, the input/output interface 909 illustrated in FIG. 38. The audio module 938 may process sound information which is input or output through, for example, a speaker 938A, a receiver 938B, an earphone 938C, a microphone 938D or the like.

The camera module 939 is a device which may photograph a still image and a dynamic image. According to an embodiment, the camera module 939 may include one or more image sensors (e.g., a front sensor or a back sensor), a lens, an Image Signal Processor (ISP) or a flash (e.g., LED or xenon lamp).

The power management module 942 may manage, for example, power of the electronic device 931. According to an embodiment, the power management module 942 may include a Power Management Integrated Circuit (PMIC), a charger Integrated Circuit (IC), or a battery or fuel gauge. The PMIC may have a wired and/or wireless charging scheme. Examples of the wireless charging method may include, for example, a magnetic resonance method, a magnetic induction method, an electromagnetic method, and the like. Additional circuits for wireless charging may further include e.g., a coil loop, a resonance circuit, a rectifier, etc. The battery gauge may measure, for example, the remaining amount of battery 943, a charging voltage and current, or temperature. The battery 943 may include, for example, a rechargeable battery and/or a solar battery.

The indicator 940 may display a specific state of the electronic device 931 or a part thereof (e.g., the AP 932), for example, a booting status, a message status, a charging status, or the like. The motor 941 may convert an electrical signal into mechanical vibrations, and may generate a vibration or haptic effect. Although not illustrated, the electronic device 931 may include a processing device (e.g., a GPU) for supporting mobile TV. The processing device for supporting mobile TV may process media data according to a standard of Digital Multimedia Broadcasting (DMB), Digital Video Broadcasting (DVB), media flow or the like.

Each of the components of the electronic device according to the present disclosure may be implemented by one or more components and the name of the corresponding component may vary depending on a type of the electronic device. In various embodiments, the electronic device may include at least one of the above-described elements. Some of the above-described elements may be omitted from the electronic device, or the electronic device may further include additional elements. Further, some of the components of the electronic device according to the various embodiments of the present disclosure may be combined to form a single entity, and thus, may equivalently execute functions of the corresponding elements prior to the combination.

Figure 40:
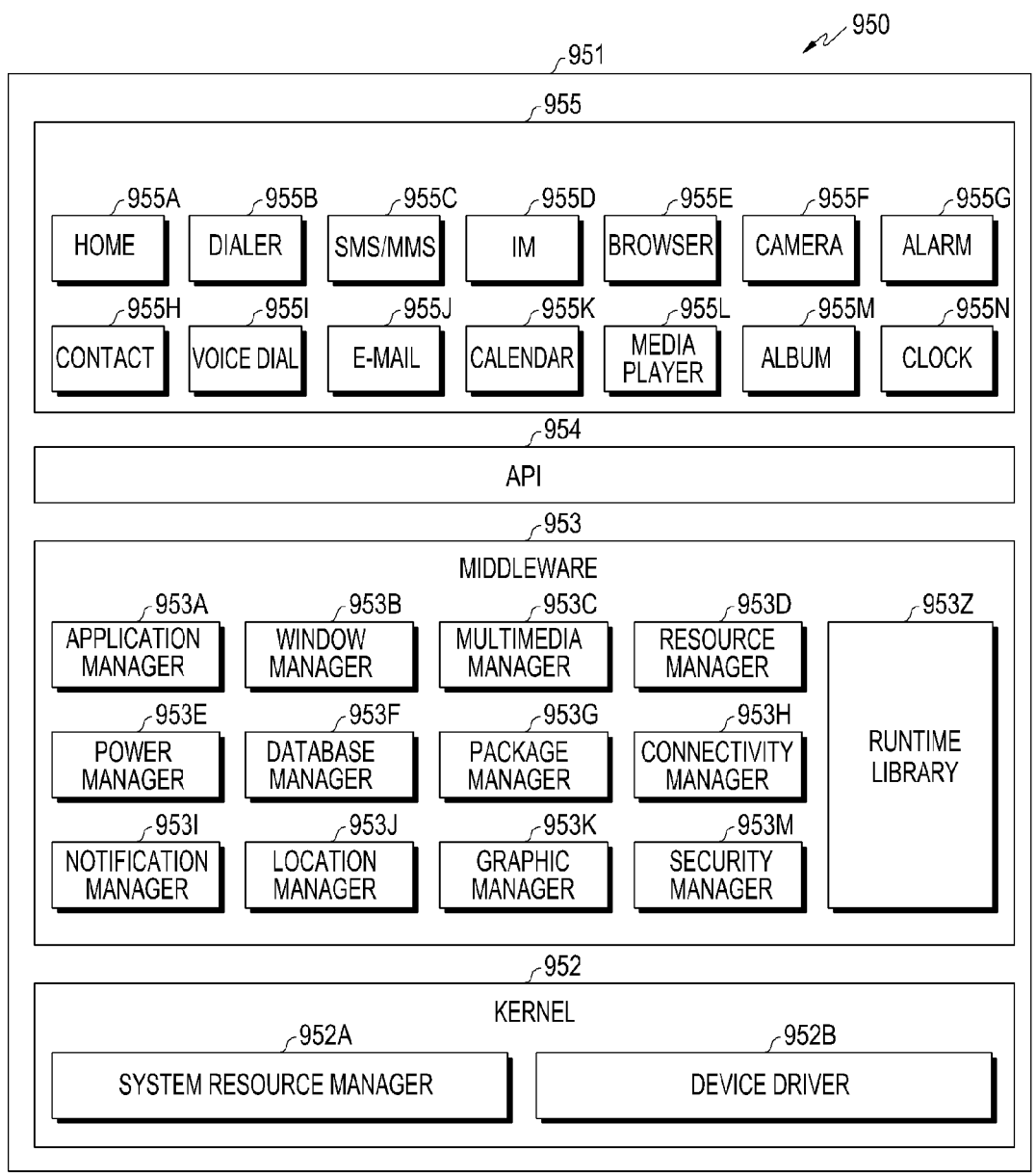
FIG. 40 is a block diagram illustrating a program module according to various embodiments.

FIG. 40 is a block diagram 950 illustrating a program module 951 according to various embodiments of the present disclosure. According to an embodiment, the program module 951 (e.g., the program 908 in FIG. 38) may include an Operating System (OS) for controlling resources related to the electronic device (e.g., the electronic device 901 in FIG. 38) and/or various applications (e.g., the applications 916 in FIG. 38) executed on the OS. The operating system may be, for example, Android, iOS, Windows, Symbian, Tizen, Bada, or the like.

The program module 951 may include a kernel 952, middleware 953, an API 954, and/or a plurality of applications 955. At least some of the program module 951 may be preloaded in the electronic device or downloaded from the server (e.g., the server 904).

The kernel 952 (e.g., the kernel 913) may include, for example, a system resource manager 952A or a device driver 952B. The system resource manager 952A may control, allocate, or collect the system resources. According to an embodiment, the system resource manager 952A may include a process manager, a memory manager, or a file system manager. The device driver 952B may include, for example, a display driver, a camera driver, a Bluetooth driver, a shared-memory driver, a USB driver, a keypad driver, a Wi-Fi driver, an audio driver, or an Inter-Process Communication (IPC) driver.

The middleware 953 may provide a function required by the applications 270 in common or provide various functions to the applications 955 through the API 954 so that the applications 955 may efficiently use limited system resources of the electronic device. According to an embodiment, the middleware 953 (e.g., the middleware 914 in FIG. 38) may include, for example, at least one of a runtime library 953Z, an application manager 953A, a window manager 953B, a multimedia manager 953C, a resource manager 953D, a power manager 953E, a database manager 953F, a package manager 953G, a connectivity manager 953H, a notification manager 953I, a location manager 953J, a graphic manager 953K, and a security manager 953M.

The runtime library 953Z may include, for example, a library module that a compiler uses in order to add new functions through a programming language while one or more of the applications 955 are being executed. The runtime library 953Z may perform input/output management, memory management, or a function for an arithmetic function.

The application manager 953A may manage, for example, a life cycle of at least one application among the applications 955. The window manager 953B may manage GUI resources used on the screen. The multimedia manager 953C may identify formats required for reproduction of various media files, and may encode or decode the media file by using a codec suitable for the corresponding format. The resource manager 953D may manage resources such as a source code, a memory, or a storage space of at least one of the applications 955.

The power manager 953E may operate together with, for example, a Basic Input/Output System (BIOS), so as to manage a battery or power and may provide power information required for the operation of the electronic device. The database manager 953F may generate, search for, or change a database to be used by at least one of the applications 955. The package manager 953G may manage installation or an update of an application distributed in a form of a package file.

For example, the connectivity manager 953H may manage wireless connections, such as WIFI or Bluetooth. The notification manager 953I may display or notify of an event such as an arrival message, an appointment, proximity notification, and the like in such a way that a user is not disturbed. The location manager 953J may manage location information of the electronic device. The graphic manager 953K may manage graphic effects to be provided to a user and user interfaces related to the graphic effects. The security manager 352 may provide various security functions required for system security or user authentication. According to an embodiment, when the electronic device (e.g., electronic device 901) has a call function, the middleware 953 may further include a telephony manager for managing a voice call function or a video call function of the electronic device.

The middleware 953 may include a middleware module for forming a combination of various functions of the aforementioned components. The middleware 953 may provide a module specialized for each type of operating system in order to provide a differentiated function. In addition, a few existing components may be dynamically removed from the middleware 953, or new components may be added to the middleware 230.

The API 954 (e.g., the API 915 in FIG. 38), which is a set of API programming functions, may be provided in a different configuration according to the OS. For example, in the case of Android or iOS, one API set may be provided for each platform. In the case of Tizen, two or more API sets may be provided for each platform.

The application 955 (e.g., the applications 916 in FIG. 38) may include, for example, one or more applications which may provide functions such as a home function 955A, a dialer 955B, an SMS/MMS 955C, an Instant Message (IM) 955D, a browser 955E, a camera 955F, an alarm 955G, a contact 955H, a voice dialer 955I, an E-mail 955J, a calendar 955K, a media player 955L, an album 955M, a clock 955N, a health care (e.g., measurement of exercise quantity or blood sugar), or provision of environment information (e.g., atmospheric pressure, humidity, or temperature information). For example, the application for providing the health care function may display information on a body composition according to a time.

According to an embodiment, the applications 955 may include an application (hereinafter, referred to as an "information exchange application" for convenience of description) supporting information exchange between the electronic device (e.g., the electronic device 901 in FIG. 38) and an external electronic device (e.g., the first electronic device 902 or the second electronic device 903 in FIG. 38). The information exchange application may include, for example, a notification relay application for transmitting specific information to the external electronic device, or a device management application for managing the external electronic device. For example, the notification relay application may include a function of transferring, to external electronic devices, such as, for example, the first electronic device 902 or the second electronic device 903, notification information generated from other applications of the electronic device 901 (e.g., an SMS/MMS application, an E-mail application, a health management application, or an environmental information application). Further, the notification relay application may receive notification information from, for example, an external electronic device and provide the received notification information to a user. Further, the application may transmit a numerical level of a body composition to a doctor while interworking with a medical institution such as a hospital and a health center. The doctor may diagnose a state of a patient through the numerical level of the body composition. The application may transmit diagnosis contents of the doctor to a user.

The device management application may manage (e.g., install, delete, or update), for example, a function for at least a part of the external electronic device (e.g., the second electronic device 903 in FIG. 38) communicating with the electronic device (e.g., turning on/off the external electronic device itself (or some elements thereof) or adjusting brightness (or resolution) of a display), applications executed in the external electronic device, or services provided from the external electronic device (e.g., a telephone call service or a message service).

According to an embodiment, the applications 955 may include an application (e.g., health management application) designated according to attributes (e.g., attributes of the electronic device such as the type of electronic device which corresponds to a mobile medical device) of the external electronic device (e.g., the first electronic device 902 or the second electronic device 903 in FIG. 38). According to an embodiment, the applications 955 may include an application received from e.g., the server 904, the first electronic device 902, or the second electronic device 903 in FIG. 38. According to an embodiment, the applications 955 may include a preloaded application or a third party application which may be downloaded from the server. Names of the elements of the program module 951, according to the above-described embodiments of the present disclosure, may change depending on the type of OS.

According to various exemplary embodiments of the present disclosure, at least some of the program module 951 may be implemented in software, firmware, hardware, or a combination of two or more thereof. At least a portion of the program module 951 may be implemented (e.g., executed) by, for example, the processor (e.g., the AP 932). At least some of the program module 951 may include, for example, a module, program, routine, sets of instructions, process, or the like for performing one or more functions.

The "module" used in various embodiments of the present disclosure may refer to, for example, a "unit" including one of hardware, software, and firmware, or a combination of two or more of the hardware, software, and firmware. The "module" may be interchangeably used with, for example, the term "unit", "logic", "logical block", "component", or "circuit". The "module" may be a minimum unit of an integrated component element or a part thereof. The "module" may be a minimum unit for performing one or more functions or a part thereof. The "module" may be mechanically or electronically implemented. For example, the "module" according to the present disclosure may include at least one of an Application-Specific Integrated Circuit (ASIC) chip, a Field-Programmable Gate Arrays (FPGA), and a programmable-logic device for performing operations which has been known or are to be developed hereinafter.

According to various embodiments, at least some of the devices (e.g., modules or functions thereof) or the method (e.g., operations) according to the present disclosure may be implemented by a command stored in a computer-readable storage medium in a programming module form. When the command is executed by one or more processors (e.g., the processor 906, in FIG. 38), the one or more processors may execute a function corresponding to the command. The computer-readable storage medium may be, for example, the memory (907 in FIG. 38).

The computer readable recoding medium may include a hard disk, a floppy disk, magnetic media (e.g., a magnetic tape), optical media (e.g., a Compact Disc Read Only Memory (CD-ROM) and a Digital Versatile Disc (DVD)), magneto-optical media (e.g., a floptical disk), a hardware device (e.g., a Read Only Memory (ROM), a Random Access Memory (RAM), a flash memory), and the like. In addition, the program instructions may include high class language codes, which may be executed in a computer by using an interpreter, as well as machine codes made by a compiler. The aforementioned hardware device may be configured to operate as one or more software modules in order to perform the operation of the present disclosure, and vice versa.

The programming module according to the present disclosure may include one or more of the aforementioned components or may further include other additional components, or some of the aforementioned components may be omitted. Operations executed by a module, a programming module, or other component elements according to various embodiments of the present disclosure may be executed sequentially, in parallel, repeatedly, or in a heuristic manner. Further, some operations may be executed according to another order or may be omitted, or other operations may be added.

As described above, a wearable body composition analyzer according to various embodiments of the present disclosure may include an induction part for inducing a secretion of bodily liquid while being in contact with the skin of a body, a collection part for collecting the secreted bodily liquid, a sensor part for detecting a body composition from the collected bodily liquid, and a wearable part to which at least one of the induction part and the collection part is detachably attached, wherein the wearable part may be worn on a body.

Further, according to various embodiments, the collection part may include a space provision part for providing a collection space in which the secreted bodily liquid is collected while being in contact with a part of the skin, and a channel part communicating with the collection space and providing a movement path through which the body composition is moved.

Further, according to various embodiments, the space provision may include a cover part having a communication opening formed therein to communicate with the movement path, a contact part extending from a lower portion of the cover part to form a closed curve so as to form the collection space, and a support part extending from the lower portion of the cover part within a closed curve constituting the contact part, wherein the support part may prevent a close contact between the cover part and the skin.

Further, according to various embodiments, the channel part may include a sensor coupling part to which the sensor part is coupled on the movement path.

Further, according to various embodiments, the channel part constituting the movement path may be made of a hydrophil material, and one end of the channel part may be made of a hydrophobic material.

Further, according to various embodiments, the sensor part may detect glucose from the bodily liquid.

Further, a wearable body composition analyzer according to various embodiments of the present disclosure may further include a driving circuit part for applying a signal to the induction part and the sensor part.

Further, according to various embodiments, the driving circuit part may include a first connection part connected to the induction part and a second connection part connected to the sensor part.

Further, according to various embodiments, the induction part includes an inductive agent for inducing the secretion of the bodily liquid, and the inductive agent may be injected into the skin by the signal applied from the driving circuit part.

Further, according to various embodiments, the sensor part includes an operation electrode operated by the signal applied from the driving circuit part, and a counter electronic arranged to be spaced apart from the operation electrode, and may detect a current by a body composition between the operation electrode and the counter electrode.

Further, according to various embodiments, the sensor part includes an auxiliary electrode arranged to be spaced apart from the operation electrode, and the auxiliary electrode may detect a current flowing between the operation electrode and the auxiliary electrode so as to determine whether there is the body composition.

Further, the wearable body composition analyzer according to various embodiments of the present disclosure may further include a body part detachably attached to the wearable part, to which the sensor part and the induction part are attached, and the plurality of attachment parts may be arranged in the circumference of the driving circuit part along a circumferential direction of the wearable part.

Further, according to various embodiments, the induction part may include a first induction part which protrudes from one surface of the attachment part and is arranged to be spaced apart from the circumference of the sensor part, and a second induction part which protrudes from one surface of the attachment part and is arranged between the first induction part and the sensor part.

Further, the wearable body composition analyzer according to various embodiments of the present disclosure may further include a washing part which is mounted to the wearable part and sprays a washing liquid to a part where the wearable part is in contact with the skin.

Further, a wearable body composition analyzer according to various embodiments of the present disclosure may include a wearable part worn on a body, a body part attached to the wearable part, an induction part mounted to the body part to induce a secretion of a bodily liquid, a collection part mounted to the body part to collect the secreted bodily liquid, and a sensor part mounted to the body part to detect the collected body composition, wherein the body part may rotate on the wearable part.

Further, the wearable body composition analyzer according to various embodiments of the present disclosure may further include a washing pad part mounted to the body part to wash the skin of the body, and a drying pad part mounted to the body part to dry the skin of the body.

Further, the wearable body composition analyzer according to various embodiments of the present disclosure may further include an introduction line that connects the collection part to the sensor part, a washing liquid supply part that injects washing liquid through the introduction line, a discharge line connected to the sensor part, and a washing liquid absorption part that absorbs the washing liquid discharged through the discharge line.

Further, according to various embodiments, the body part may include a first body part attached to the wearable part, a driving part mounted to the first body part to provide a rotation force, and a second body part rotated by the driving part.

Further, the sensor module according to various embodiments of the present disclosure may include a first insertion part detachably attached to the induction part for inducing the secretion of the bodily liquid while being in contact with the skin of a body, a detection part provided on the first insertion part, and a second insertion part detachably attached to the driving circuit part for applying a signal for inducing the secretion of the bodily liquid to the induction part, wherein the detection part may detect a body composition from the bodily liquid collected by the induction part.

Further, the wearable body composition analyzer including the sensor module according to various embodiments of the present disclosure may include a wearable part detachably attached to at least one of the induction part the driving circuit part while being worn on a body.

While the present disclosure has been shown and described with reference to certain embodiments thereof, it will be understood by those skilled in the art that various changes in form and details may be made therein without departing from the spirit and scope of the present disclosure as defined by the appended claims.

What is claimed is:

1. A wearable body composition analyzer comprising:
    an induction circuit configured to induce a secretion of a bodily liquid from a body part;
    a collector configured to collect the bodily liquid secreted;
    a sensor configured to detect a body composition from the bodily liquid collected by the collector; and
    a wearable part configured to detachably receive each of the induction circuit, the collector, and the sensor, so that the induction circuit, the collector, and the sensor are slidingly received in a groove in the wearable part so as to be removable when desired,
    wherein the wearable part is configured to be worn on the body;
    wherein the analyzer further comprises a driving circuit and an induction body part providing a support groove, wherein the driving circuit comprises a protrusion part, and wherein the protrusion part is configured to connect the driving circuit with the induction body part when the protrusion part is inserted into the support groove of the induction body part.

2. The wearable body composition analyzer of claim 1, wherein the collector comprises: a space provision part that provides a collection space in which the bodily liquid secreted is collected while the space provision part is in contact with the body part; and a movement path part communicating with the collection space, through which the bodily liquid is moved.

3. The wearable body composition analyzer of claim 2, wherein the space provision part comprises: a cover part that has a communication opening formed therein to communicate with the movement path part; a contact part that extends from a lower portion of the cover part to be in contact with the body part, and constitutes a closed curve to form the collection space; and a support part that extends from the lower portion of the cover part within the closed curve constituting the contact part, wherein the support part prevents a close contact between the cover part and the body part.

4. The wearable body composition analyzer of claim 2, wherein the movement path part comprises a sensor coupling part to couple to the sensor.

5. The wearable body composition analyzer of claim 2, wherein the movement path part is made of a hydrophilic material and one end of the movement path part is made of a hydrophobic material.

6. The wearable body composition analyzer of claim 1, wherein the sensor is configured to detect glucose from the bodily liquid.

7. The wearable body composition analyzer of claim 1, wherein the induction circuit comprises a driving circuit that also provides a signal to the sensor.

8. The wearable body composition analyzer of claim 7, wherein the driving circuit comprises:
    a first connection circuit connected to the induction circuit; and
    a second connection circuit connected to the sensor.

9. The wearable body composition analyzer of claim 7, wherein the induction circuit comprises an inductive agent that induces the secretion of the bodily liquid, wherein the inductive agent is injected into the body part by the signal applied from the driving circuit.

10. The wearable body composition analyzer of claim 7, wherein the sensor comprises:
    an operation electrode operated by the signal applied from the driving circuit; and
    a counter electrode arranged to be spaced apart from the operation electrode,
    wherein the sensor is configured to detect a current by a body composition between the operation electrode and the counter electrode.

11. The wearable body composition analyzer of claim 10, wherein the sensor comprises an auxiliary electrode arranged to be spaced apart from the operation electrode, and the auxiliary electrode is configured to determine whether there is bodily liquid by detecting the current flowing between the operation electrode and the auxiliary electrode.

12. The wearable body composition analyzer of claim 7, further comprising a plurality of attachment parts detachably attached to the wearable part, to which the sensor part and the induction circuit are attached, wherein the plurality of attachment parts are arranged in a circumference of the driving circuit part along a circumferential direction of the wearable part.

13. The wearable body composition analyzer of claim 12, wherein the induction circuit comprises: a first induction part which protrudes from one surface of the attachment part and is arranged to be spaced apart from the circumference of the sensor; and a second induction part which protrudes from one surface of the attachment part and is arranged between the first induction part and the sensor part.

14. The wearable body composition analyzer of claim 12, further comprising a washing part mounted to the wearable part to spray washing liquid at a part where the attachment part is in contact with the body part.

* * * * *